United States Patent [19]

Fontayne et al.

[11] Patent Number: 5,376,098

[45] Date of Patent: Dec. 27, 1994

[54] FRAGMENTABLE ANASTOMOSIS RING APPLIER

[75] Inventors: Diego Fontayne, Norwalk; Henry Bolanos, East Norwalk; John C. Robertson, Bloomfield; Timothy O. Van Leeuwen, Brookfield; Thomas A. Pelletier, Wallingford; Stephen W. Gerry, Bethel, all of Conn.

[73] Assignee: United States Surgical Corporation, Norwalk, Conn.

[21] Appl. No.: 959,152

[22] Filed: Oct. 9, 1992

[51] Int. Cl.⁵ .............................................. A61B 17/00
[52] U.S. Cl. .................................. 606/153; 606/151; 606/170; 30/316
[58] Field of Search ............... 606/167, 170, 171, 179, 606/180, 151, 153; 227/19, 175, 179–181; 30/316, 361

[56] References Cited

U.S. PATENT DOCUMENTS

| D. 271,994 | 12/1983 | Noiles et al. | |
|---|---|---|---|
| D. 273,041 | 3/1984 | Noiles et al. | |
| 606,511 | 5/1898 | Buckles | 30/316 |
| 3,193,165 | 7/1965 | Akhalaya et al. | |
| 3,552,626 | 1/1971 | Astafiev et al. | |
| 3,593,903 | 7/1971 | Astafiev et al. | |
| 3,765,282 | 10/1973 | Crain, Jr. | 30/316 |
| 4,207,898 | 6/1980 | Becht | |
| 4,277,891 | 7/1981 | Dick | 30/316 |

(List continued on next page.)

FOREIGN PATENT DOCUMENTS

| 1136020 | 11/1982 | Canada . |
| 0152382 | 8/1985 | European Pat. Off. . |
| 0503689 | 9/1992 | European Pat. Off. . |
| 0517488 | 12/1992 | European Pat. Off. . |
| 7930018 | 12/1979 | France . |
| 1509052 | 9/1989 | U.S.S.R. . |
| WO8900406 | 1/1989 | WIPO . |
| WO9006085 | 6/1990 | WIPO . |

OTHER PUBLICATIONS

Article entitled "Clinical Application of a New Compression Anastomotic Device for Colorectal Surgery" by Carlo Rebuffat, M.D., et al. published in the American Journal of Surgery, vol. 159, pp. 330–335, Mar. 1990.

Article entitled "A New Mechanical Device for Circular Compression Anastomosis" by R. Rosati M.D., et al. presented at the First Surgical Clinic-University of Milan, Italy, Ann-Surg., pp. 245–252, Mar. 1988.

"Information Booklet for an Auto Suture, Surgical Stapling Instrument," United States Surgical Corporation, 1984.

Primary Examiner—Stephen C. Pellegrino
Assistant Examiner—Jeffrey A. Schmidt

[57] ABSTRACT

A novel surgical instrument suitable for insertion and assembly of multi-ring compression devices for circular anastomosis of tubular tissue sections including a body having means to support and align the rings, means for clamping the rings around the free ends of the tissue sections, means for coring away excess clamped tissue and the centers of the rings, separate means for releasing the clamped rings from the instrument and dwell means to delay releasing the rings until after the coring operation is complete. The dwell means consists of an external cap containing separate and coaxial elements for the coring means and the releasing means which are provided with a series of recesses and a plurality of shifter keys to separate the operation of coring from the separate operation of releasing the assembled multi-ring compression device from the instrument. The instrument may additionally include means for detaching a portion of the support means to facilitate installation and alignment, and a safety to ensure safe operation and interchangeable knife blades.

37 Claims, 16 Drawing Sheets

U.S. PATENT DOCUMENTS

| | | |
|---|---|---|
| 4,304,236 | 12/1981 | Conta et al. . |
| 4,351,466 | 9/1982 | Noiles . |
| 4,379,457 | 4/1983 | Gravener et al. . |
| 4,473,077 | 9/1984 | Noiles et al. . |
| 4,485,817 | 12/1984 | Swiggett . |
| 4,488,523 | 12/1984 | Shichman . |
| 4,573,468 | 3/1986 | Conta et al. . |
| 4,576,167 | 3/1986 | Noiles . |
| 4,598,712 | 7/1986 | Rebuffat et al. . |
| 4,603,693 | 8/1986 | Conta et al. . |
| 4,606,343 | 8/1986 | Conta et al. . |
| 4,646,745 | 3/1987 | Noiles . |
| 4,667,673 | 5/1987 | Li . |
| 4,681,108 | 7/1987 | Rosati et al. . |
| 4,752,024 | 6/1988 | Green et al. . |
| 4,776,506 | 10/1988 | Green . |
| 4,817,847 | 4/1989 | Redtenbacher et al. . |
| 4,893,622 | 1/1990 | Green et al. . |
| 4,907,591 | 3/1990 | Vasconcellos et al. . |
| 4,917,114 | 4/1990 | Green et al. . |
| 4,931,057 | 6/1990 | Cummings et al. . |
| 4,957,499 | 9/1990 | Lipatov et al. . |
| 4,964,863 | 10/1990 | Kanshin et al. . |
| 4,966,602 | 10/1990 | Rebuffat et al. . |
| 5,005,749 | 4/1991 | Aranyi . |
| 5,119,983 | 6/1992 | Green et al. ............ 227/19 |
| 5,122,156 | 6/1992 | Granger et al. . |
| 5,139,513 | 8/1992 | Segato . |

FIG.14a
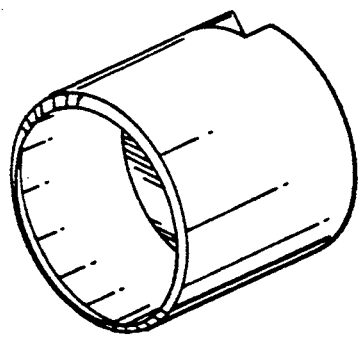
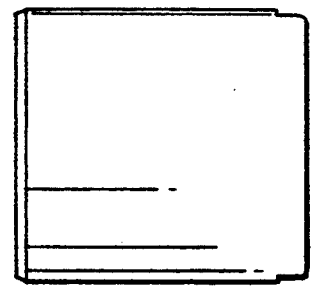
FIG.14aa
FIG.14c
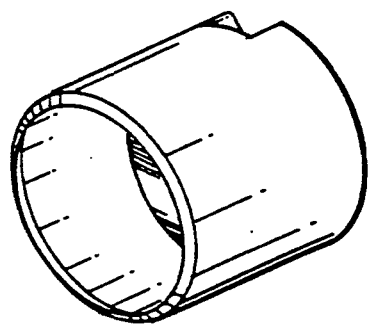
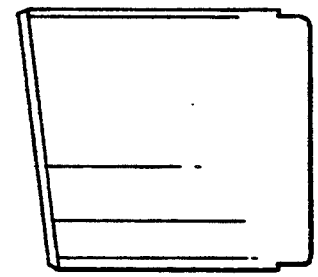
FIG.14cc
FIG.14b
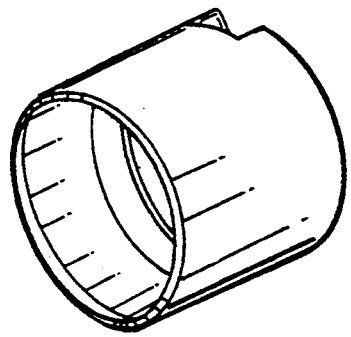
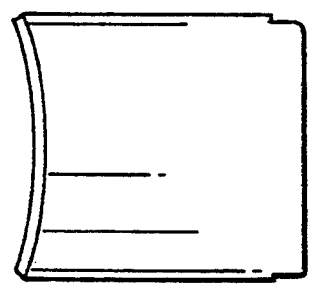
FIG.14bb

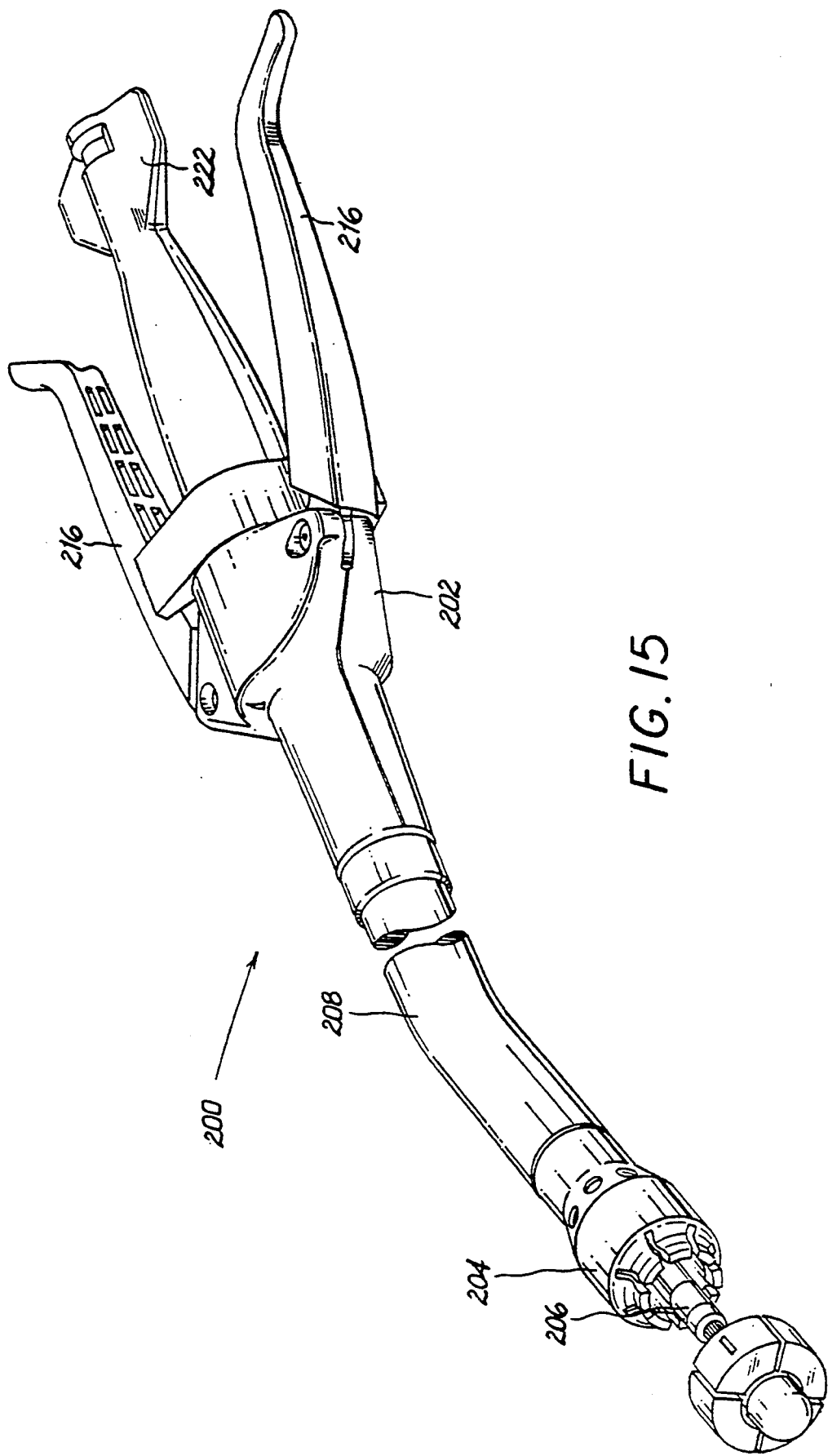

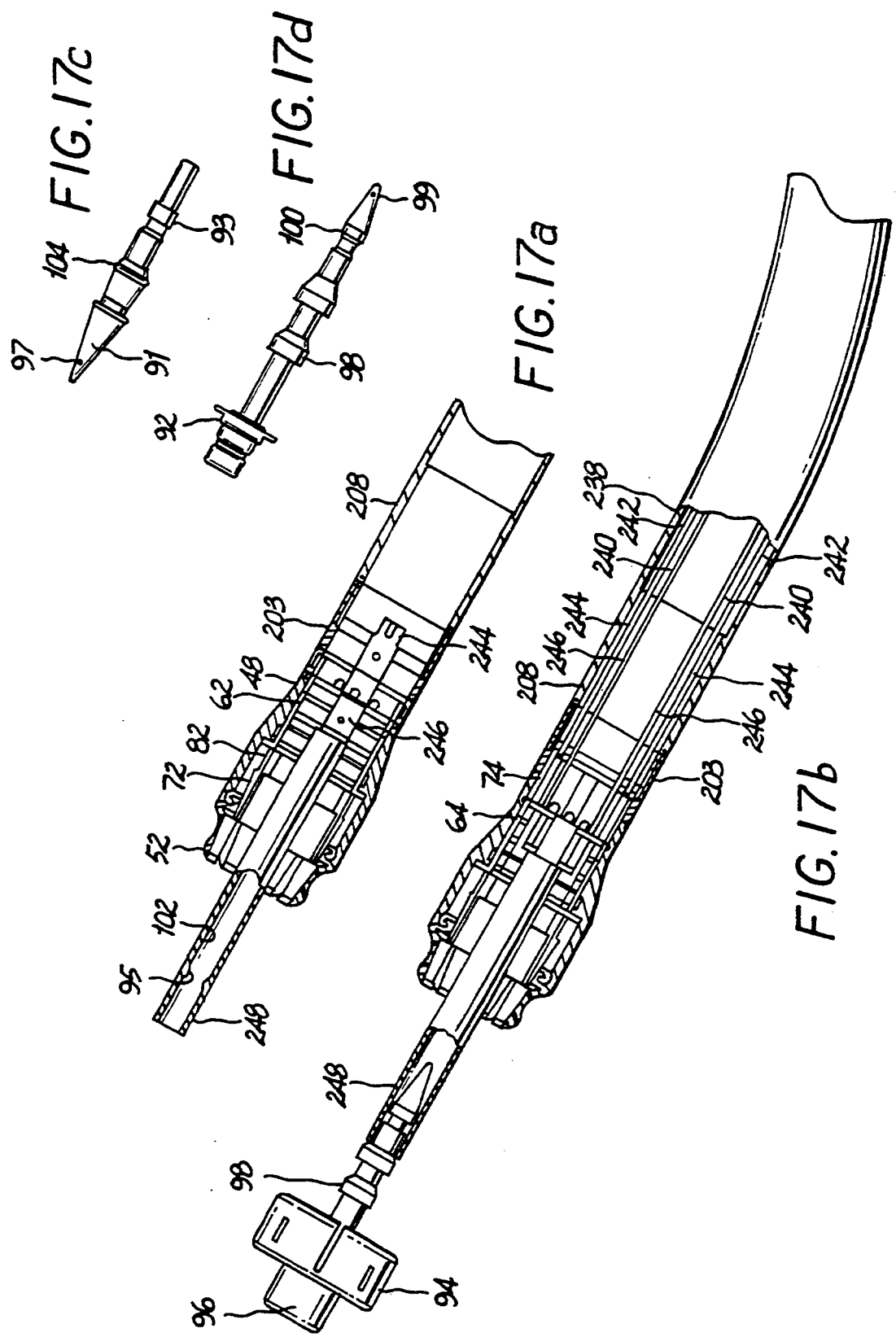

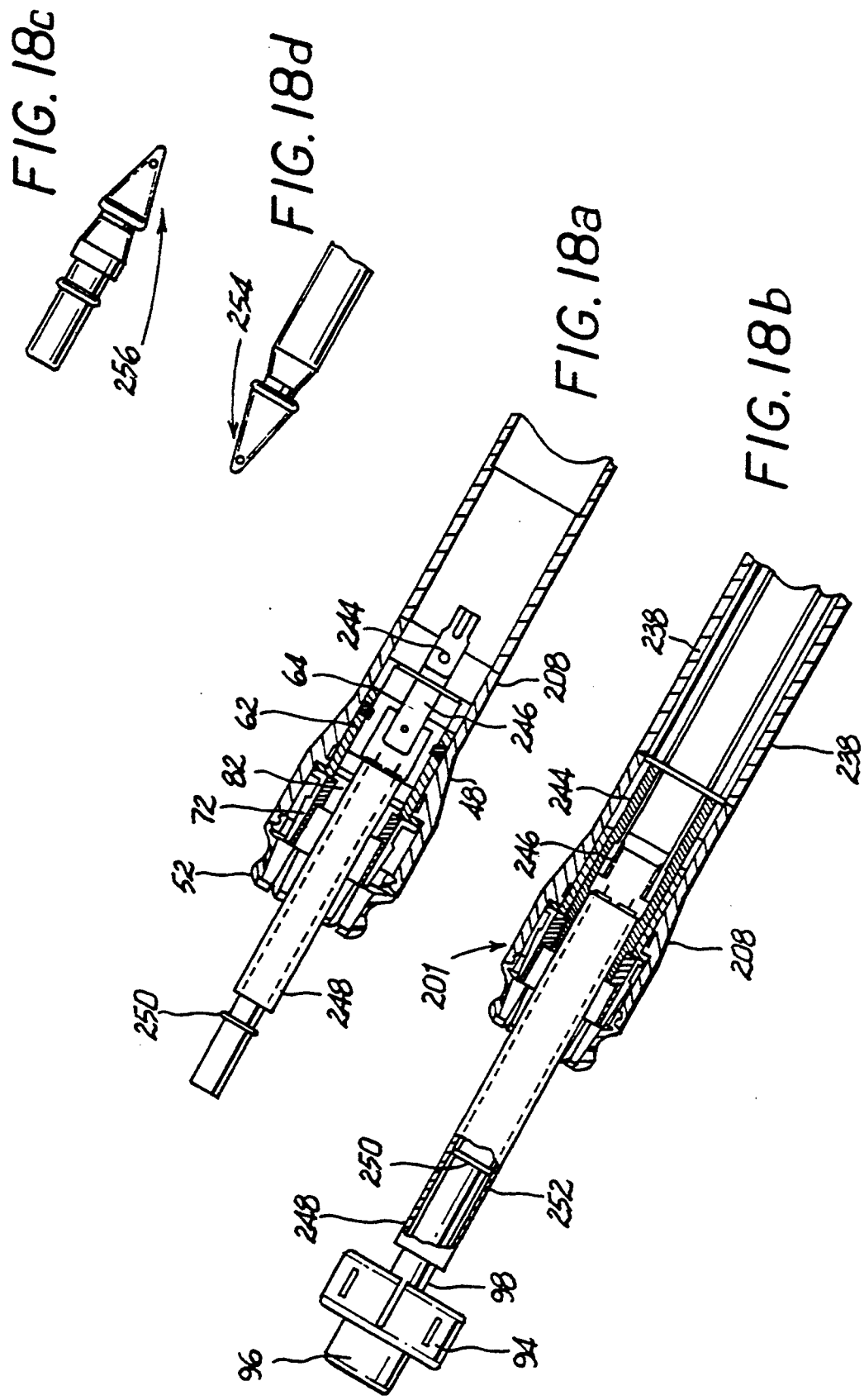

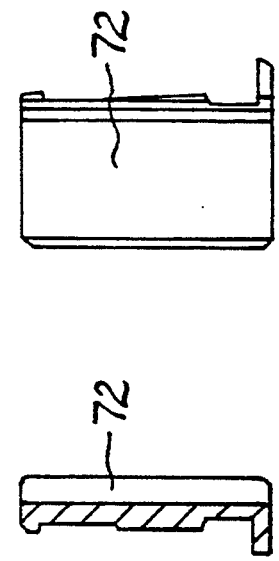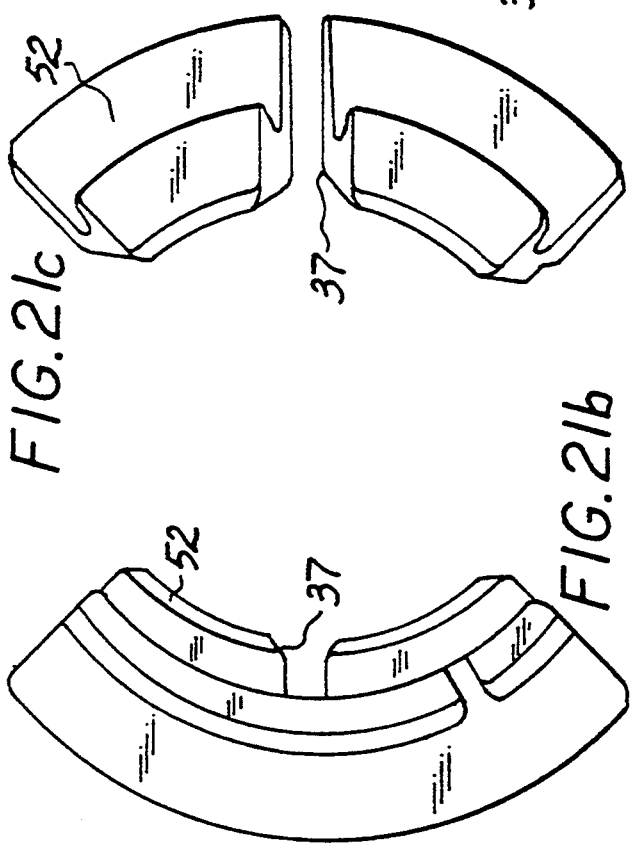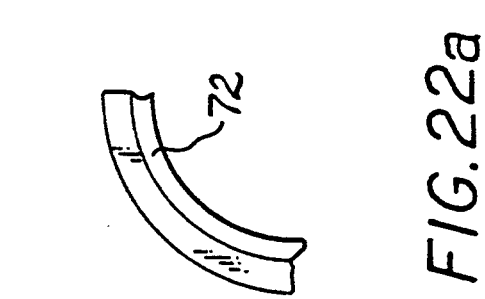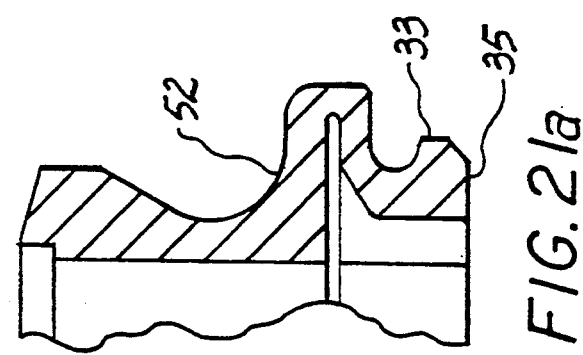

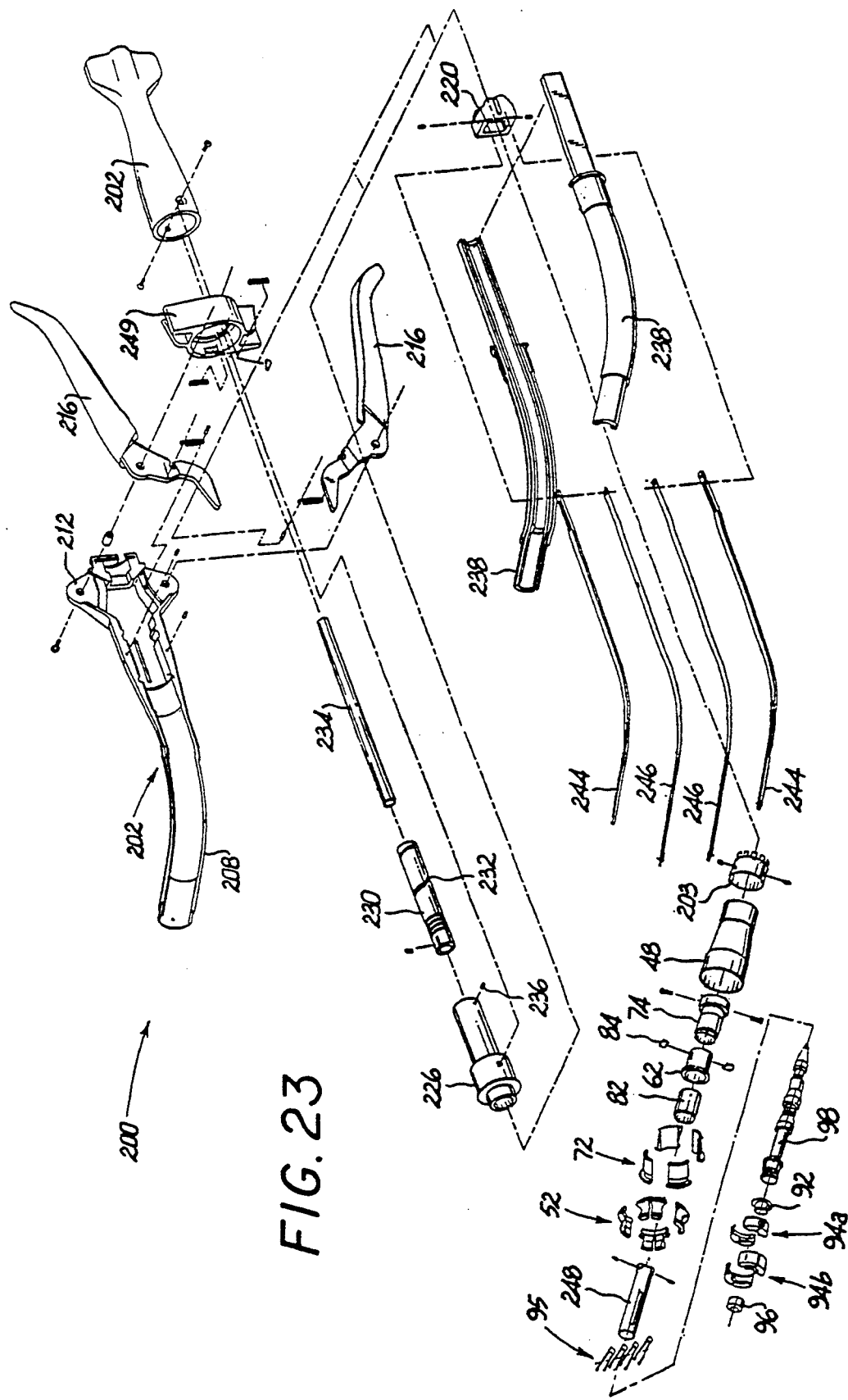

FRAGMENTABLE ANASTOMOSIS RING APPLIER

BACKGROUND OF THE INVENTION

1. Field of the Invention

The present invention relates to surgical instruments used to perform circular anastomosis of tubular tissue sections and, more particularly, to a surgical instrument suitable for installation of multi-ring compression devices for circular anastomosis of tubular tissue sections.

2. Description of Related Art

Some surgical procedures, such as repair of the colon, require the joining of two rather large sections of tubular tissue. During these procedures, a diseased area of tissue is excised leaving two free ends of healthy tissue to be joined. Some known methods of joining the tissues include stapling or suturing the ends together. A more recent advancement in the art, called a multi-ring compression device, is used to clamp the free ends of the tissue between a series of interlocking rings whose centers are then cut away.

Typically, a multi-ring compression device consists of the outer ring assembly which fits over an intermediary ring. The two rings are then locked together by inserting an inner ring in the intermediary ring which locks in place.

In use the free open ends of tissue are captured between the outer ring assembly and the intermediary ring. The entire assembly is then locked together by insertion of the inner ring. The inner core of the ring assembly is then cut away along with any excess tissue. The clamped tissue within the rings is deprived of blood causing necrosis to take place. The outer tissue heals while the necrosised inner tissues and clamps are detached and expelled by the body. Newer clamps or compression rings, such as those shown in U.S. Pat. No. 4,966,602, have a fragmentable structure which enhances the bodies ability to expel the device.

Various surgical instruments have been developed to install the multi-ring compression devices. One known surgical instrument used to install the compression rings is shown in U.S. Pat. No. 4,681,108 to Rosati et al. This instrument generally comprises a cylindrical housing having means for aligning the rings within the tubular tissue sections, driving means for clamping the rings together in locking arrangement around the tissue sections and cutting means for removing excess tissue ends and detaching the instrument from the rings. In the Rosati et al. instrument, the cutting means consists of an advancing circular blade which both cuts the tissue and rings and pushes the rings free of the instrument in one continuous stroke.

Another known instrument for installing multi-ring compression devices is shown in U.S. Pat. No. 4,907,591 to Vasconcellos et al. This instrument includes such features as a rotating cutting blade and locking means to isolate the operation of aligning and clamping the rings from the separate continuous operation of cutting the excess tissue and freeing the instrument from the tissue.

SUMMARY AND OBJECTS OF THE INVENTION

The ring applier of the present invention is a novel surgical instrument suitable for insertion and assembly of multi-ring compression devices for circular anastomosis of tubular tissue sections. The instrument comprises a body having means to support and align the rings, means for clamping the rings around the free ends of the tissue sections, means for coring away excess clamped tissue and the centers of the rings, separate means for releasing the clamped rings from the instrument and dwell means to delay releasing the rings until after the coring operation is complete. The instrument may additionally include means for detaching a portion of the support means to facilitate installation and alignment, safety means to ensure safe operation and means for interchangeably supplying various knife blade profiles.

In a preferred embodiment of the invention the dwell means consists of an external cap containing separate and coaxial elements for the channeling means and the releasing means. The external cap, channeling and releasing elements are provided with a series of recesses which, in cooperation with a plurality of shifter keys, act to separate the operations of coring the excess material and ring centers from the separate operation of releasing the assembled and cored rings from the instrument.

In another embodiment of the invention the support means for supporting the outer ring assembly is detachable from the rest of the instrument. By detaching the outer ring and its support, it is more easily placed in a free open end of tubular tissue. The instrument can then be inserted in the opposing open end of tissue and thereafter reattached to the outer ring support means.

In a further embodiment of the invention the clamping means includes a handle which is rotatable with respect to said support means. A cam having a variable helical depression is attached to the support means and slidably supported within the handle such that rotation of the handle moves the cam within the handle. Preferably the variable helical depression in the cam is initially of a slow rate of twist to provide rapid initial approximation of the rings and of a rapid rate of twist towards the end of the cam travel to provide slower more precise approximation and increased torque for final clamping of the rings.

Thus it is an object of the present invention to provide a novel surgical instrument capable of delaying the release of an assembled multi-ring compression device until after a coring operation has been completed.

It is a further object of the invention to provide novel means of detaching an outer ring support from the main body of the device to facilitate installation and alignment of the device.

It is a still further object of the invention to provide cutting means having various interchangeable blade profiles.

Yet another objection of the invention is to provide a safety device to prevent the instrument from being operated prematurely.

Other novel features and objects of the invention will become evident from the following detailed description of the invention.

BRIEF DESCRIPTION OF THE DRAWINGS

Preferred embodiments of the invention are described hereinbelow with reference to the drawings wherein:

FIGS. 14 (a-c) are views of various knife blade profiles;

FIG. 15 is a perspective view showing an alternate double handle embodiment of the present invention;

FIGS. 17(a-d) are top and side detail views of one variation of the external cap including associated trocar tip and center rod;

FIGS. 18 (a-d) are detail views of other varying external cap portions of the alternative embodiment incorporating another variation of the detachable outer ring support and associated trocar tips;

FIGS. 21 (a-d) are detail views of an intermediate ring;

FIGS. 22 (a-d) are detail views of an inner ring; and

FIG. 23 is an exploded perspective view of the alternate embodiment of the invention.

DETAILED DESCRIPTION OF THE INVENTION

Figure 1:
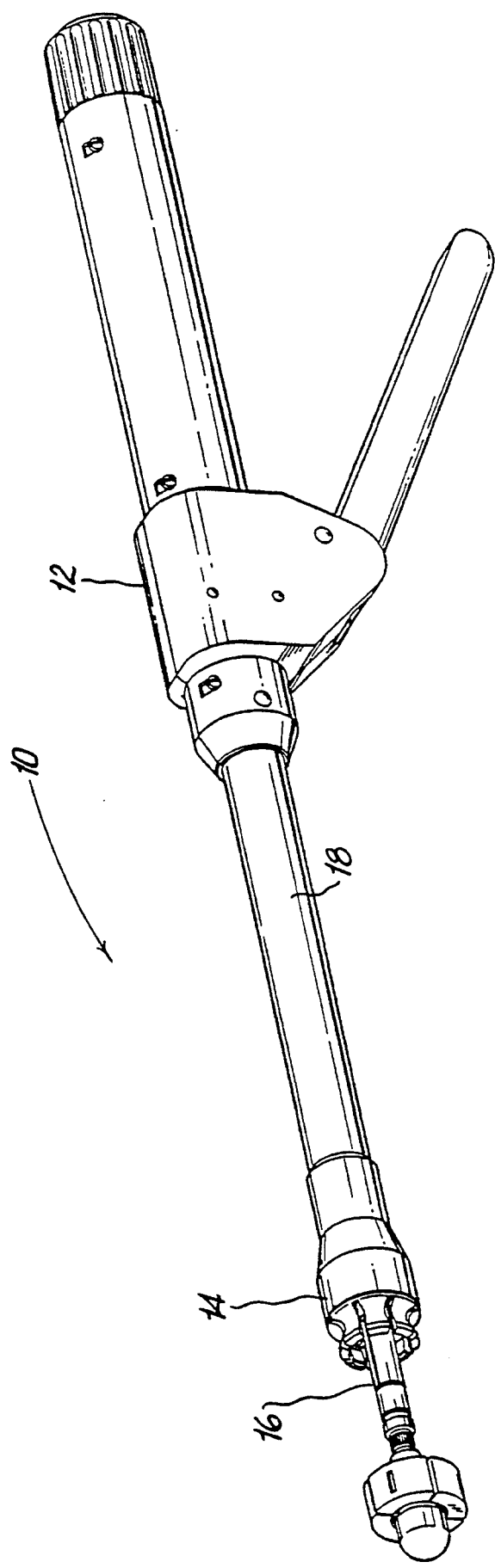
FIG. 1 is an overall perspective view of one embodiment of the present invention.

With reference now to the drawings wherein like numerals represent identical parts throughout the several views, and more particularly with reference to FIG. 1, the ring applier 10 generally includes a body portion 12, a head portion 14 and a retractor portion 16 extending through body portion 12 and head portion 14. An external tube 18 joins head portion 14 to body portion 12.

Figure 2:
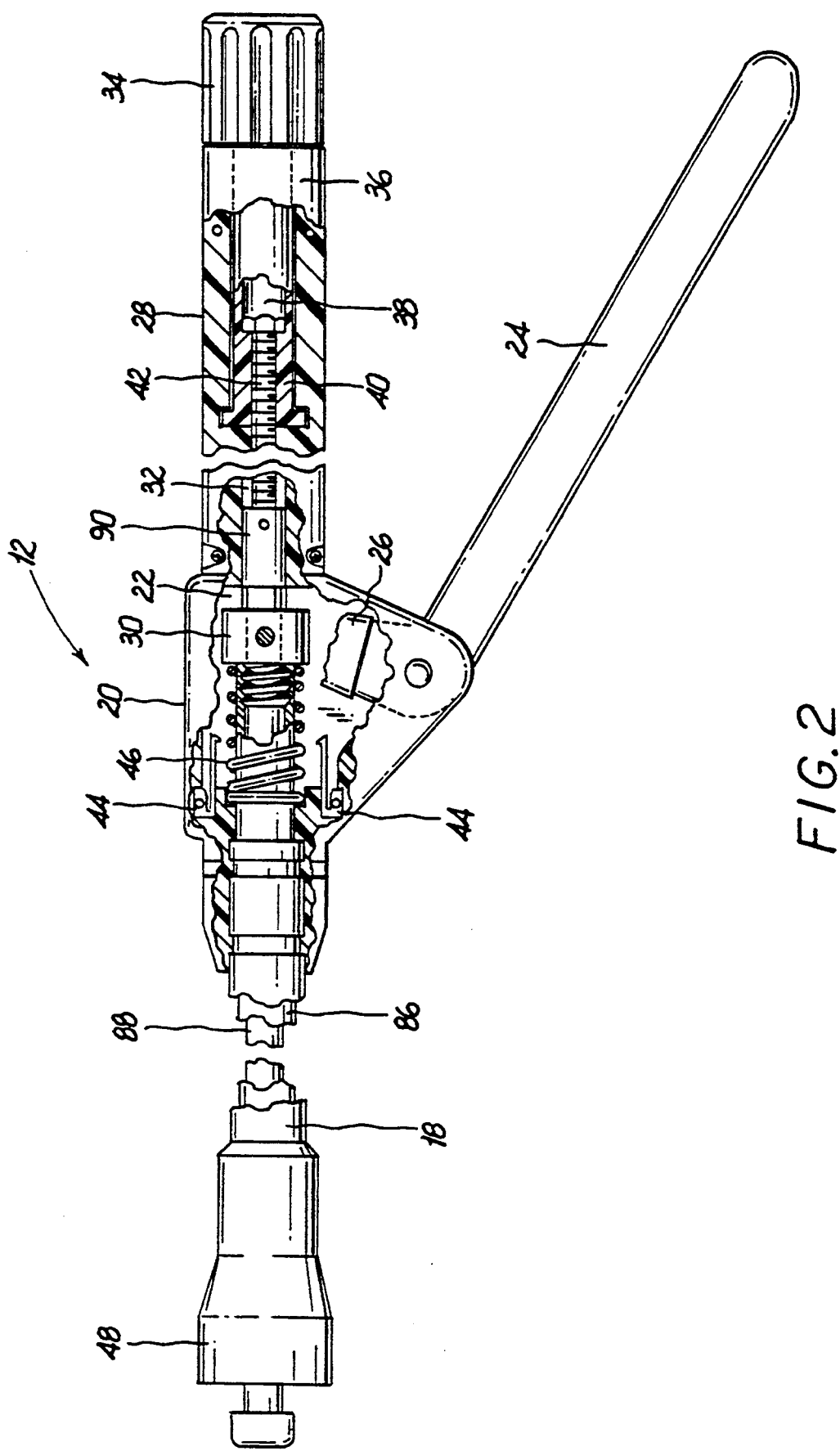
FIG. 2 is an enlarged side detail view of the handle portion of one embodiment of the present invention.

As shown in FIG. 2, body portion 12 further includes a saddle member 20 having a bore 22 therethrough, an L-shaped handle 24 pivotably mounted on saddle member 20 and having an end 26 extending into bore 22, and a tail member 28 extending outward from saddle member 20. Saddle member 20 includes a threaded collar 30 slidably disposed within bore 22 and pivotably connected to inward extending end 26 of handle 24 such that movement of handle 24 slides collar 30 within saddle bore 22. It is further contemplated to provide locking springs 44 designed to hold collar 30 at the end of its forward travel. Saddle member 20 further includes a return spring 46 for biasing collar 30 rearward within saddle bore 22.

Tail member 28 extends outward from saddle member 20 and defines a bore 32 coaxial and communicative with saddle bore 22. A clamp knob 34 is rotatably suspended at one end 36 of tail member 28 and has a bore 38 coaxial with tail bore 32. Knob 34 has a threaded base section 40 in which a threaded shaft 42 is slidably suspended within bore 38 and in threaded engagement with knob 34 such that turning knob 34 moves shaft 42 within tail bore 32.

The multi-ting compression devices used in connection with ring applier 10 generally include a plurality of interlocking rings for clamping tissue therebetween. Typically these devices consist of an outer ring 94 and an intermediary ring 52 between which the tissue is clamped and an inner ring 72 for locking insertion into intermediary ring 52. The insertion of the inner ring 72 forces outward biased edges of the intermediary ring 52 against inside edges of the outer ring 94 for a press-fit connection. When the inner ring 72 is fully seated within the intermediary ring 52, an outward facing lip of the inner ring 72 locks into place on an annular recess on an inside edge of the intermediary ring 52 thus locking the entire assembly together.

Turning now to FIGS. 19-22, a preferred embodiment of the multi-ring compression device consists of fragmentable ring assemblies. The outer ring assembly 94 consists of a male fragmentable ring 94a (FIGS. 20 (a-e)), having a shoulder 21 on a rim 23 thereof, which fits over a similar female fragmentable ring 94b (FIGS. 19(a-e)). Rings 94a and 94b are each molded in two side-by-side halves to facilitate manufacture. Each half includes a semi-circular central hub 25 to allow capture on one end of ring applier 10. Rather than provide uniform hub thickness thin ribs 27 are incorporated into relatively less thick region of the hub 25. The ribs and less thick region make it easier for hub 25 to be cut free from the body and ring applier 10 as described hereinbelow. The sectional areas of the first ring are offset from the sectional areas of the second ring, the two rings being held together by an overlapping series of projections 29 on ring 94a and recesses 31 on ring 94b. Preferably, the projections 29 on ring 94a and recesses 31 on ring 94b are aligned with the molding plane to facilitate molding. The intermediary fragmentable ring 52 is fully sectioned and has an annular projection 33 at a base 35 thereof for mounting on ring applier 10. Slots 37 in the base projection facilitates ejection of the ring assembly from ring applier 10. The locking inner fragmentable ring 72 is also sectioned into four pieces and has male and female sides so the pieces can lock together. The preferred version is more easily molded in the manufacturing process than other known versions and incorporates fillets (internal) and radii (external) on all parts to avoid sharp corners.

Figure 4:
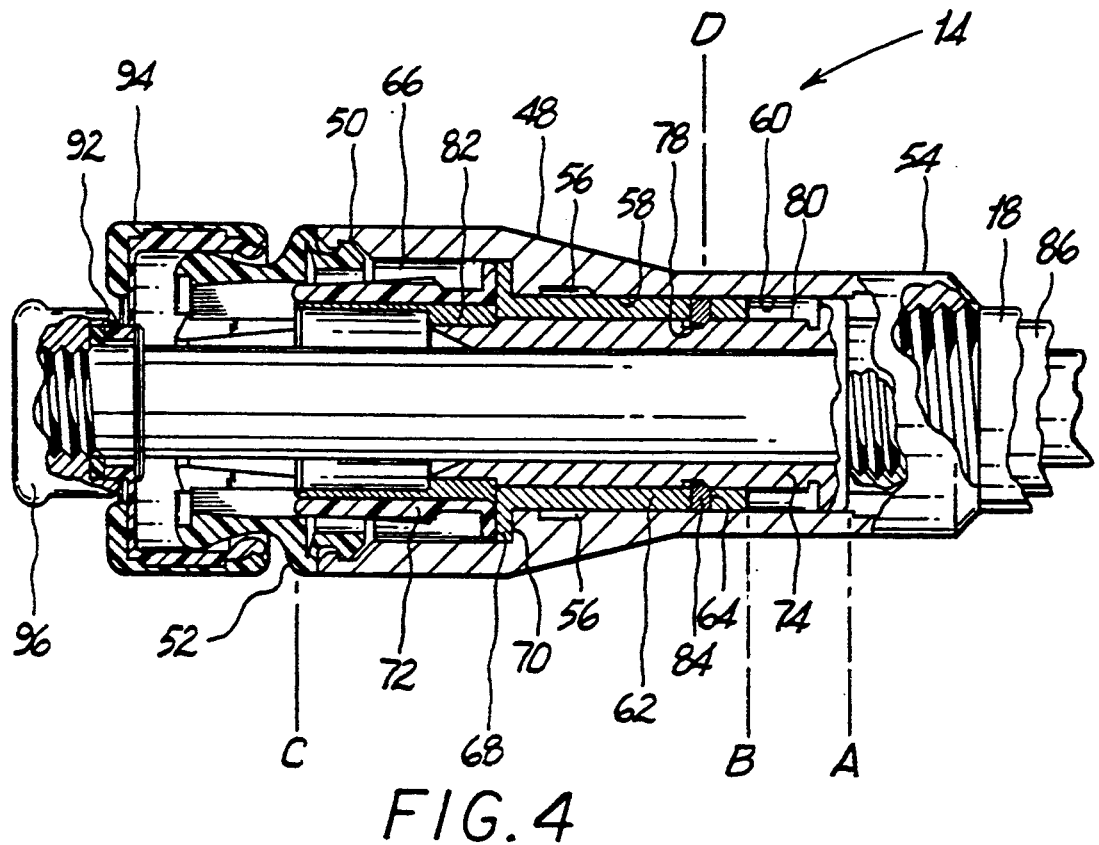
FIG. 4 is an enlarged side detail view of the head portion of the instrument of FIG. 1 showing retraction of an outer ring over an intermediary ring.

Referring now to FIG. 4 head portion 14 comprises an external cap 48 having a grooved distal end 50 for support of intermediary ring 52 and is threadably engagable with external tube portion 18 at a proximal end 54 of cap 48 thereof. External cap 48 further includes a plurality of dwell recesses 56 located on an inner surface 58 of external cap 48 and disposed within a restricted bore section 60 of external cap 48. A pusher 62 having shifter key channels 64 is slidably disposed within an enlarged bore area 66 of external cap 48 and has a circumferential flange 68 at a distal end which abuts a restricted edge 70 of restricted bore section 60. Pusher 62 slidably supports inner ring 72.

A knife holder 74 having a circumferential flange 76 at a proximal end is slidably disposed within pusher 62. Knife holder 74 further includes a plurality of shifter key recesses 78 on an outer surface 80 and means for support of a circular knife blade 82 affixed to a distal end of knife holder 74. A plurality of shifter keys 84 reside in shifter key channels 64.

Figure 8A:
FIGS. 8a and 8b are side and top detail views of the shifter keys.
Figure 8B:
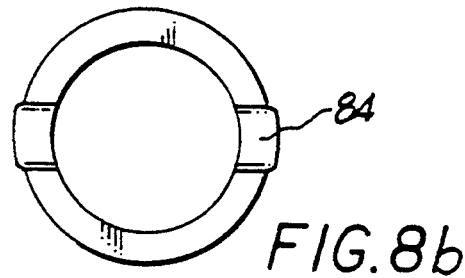

Referring to FIGS. 8a and 8b, in the preferred embodiment, shifter keys 84 have a generally trapezoidal cross section along an arcing longitudinal axis. However, one skilled in the art will appreciate that other cross-sectional configurations may be substituted therefor.

A knife tube 86 is coaxial with and slidably supported within external tube 18. (See FIGS. 2 and 3.) Knife tube 86 is threadably engaged with collar 30 at a proximal end and threadably engaged with knife holder 74 at a distal end thereof such that movement of handle 24 causes knife holder 74 to slide within pusher 62 thereby transmitting the movement of handle 24 to pusher 62.

Figure 3:
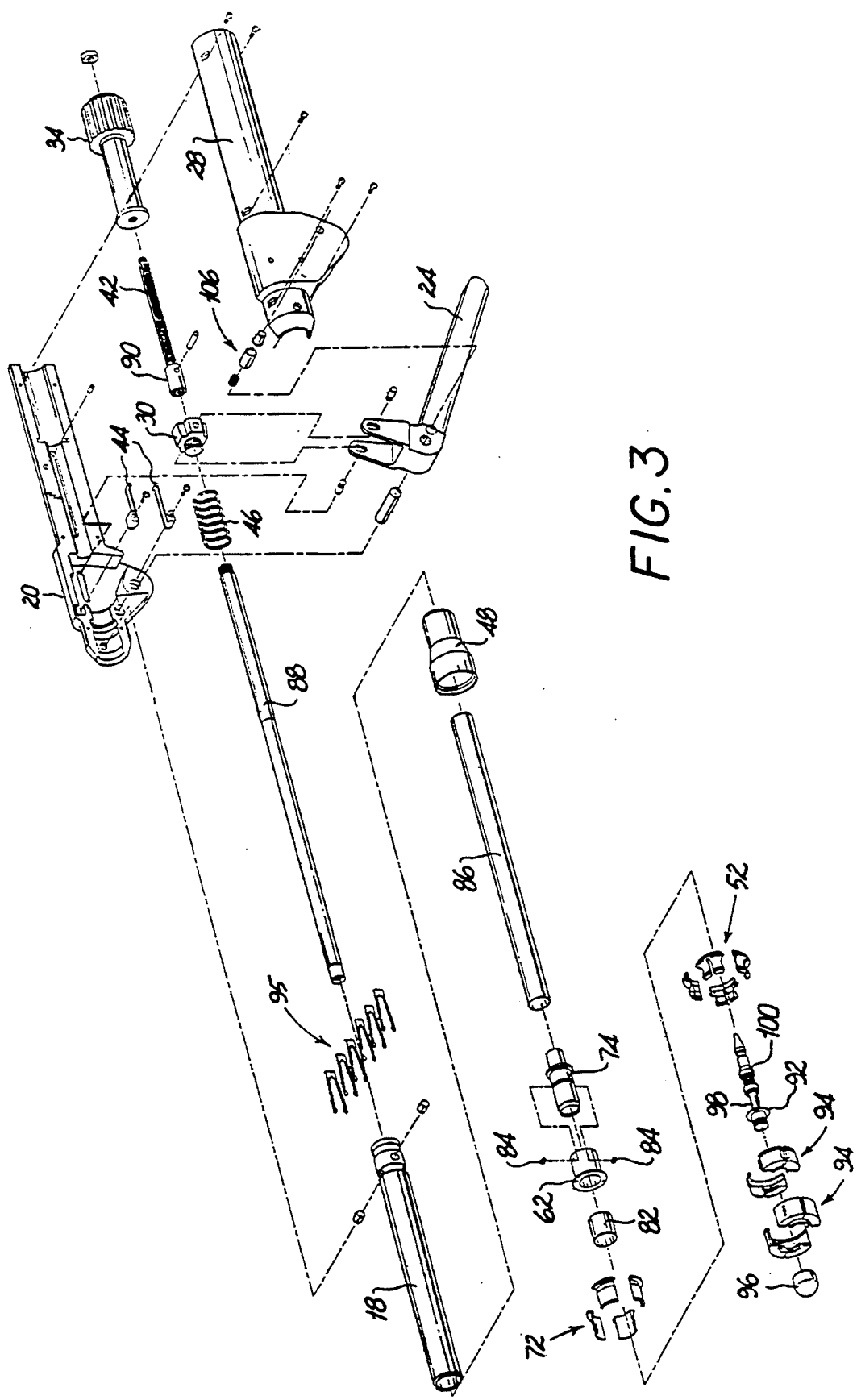
FIG. 3 is an exploded perspective view of one embodiment of the present invention.

Referring to FIG. 3 retractor portion 16 includes a clamp rod 88 affixed at a proximal end to a coupling 90 to transmit motion of shaft 42 through tube 18 to coupling 90. Coupling 90 resides in tail member 28 and is engagable with threaded shaft 42. Clamp rod 88 has an annular projection 92 at a distal end thereof for carrying outer ring 94. Clamp rod 88 further includes a threaded retainer 96 to hold outer ring 94 in place against annular projection 92.

In a preferred embodiment of the invention retainer 96 and annular projection 92 are located on a center rod 98 which is detachable from said clamp rod 88. Referring to FIG. 3, center rod 98 has an annular projection 100 disposed proximally along its length. At the extreme proximal end of center rod 98 is a pointed tip 99 having a hole 101 therein for attachment of a suture or thread. In this preferred embodiment clamp rod 88 is hollow at a distal end thereof. An annular depression 102 is located on an inner surface of clamp rod 88 and is supplied with a plurality of leaf springs 95 biased inward into depression 102 for snap-fit receipt of annular projection 100 on center rod 98.

Figure 10:
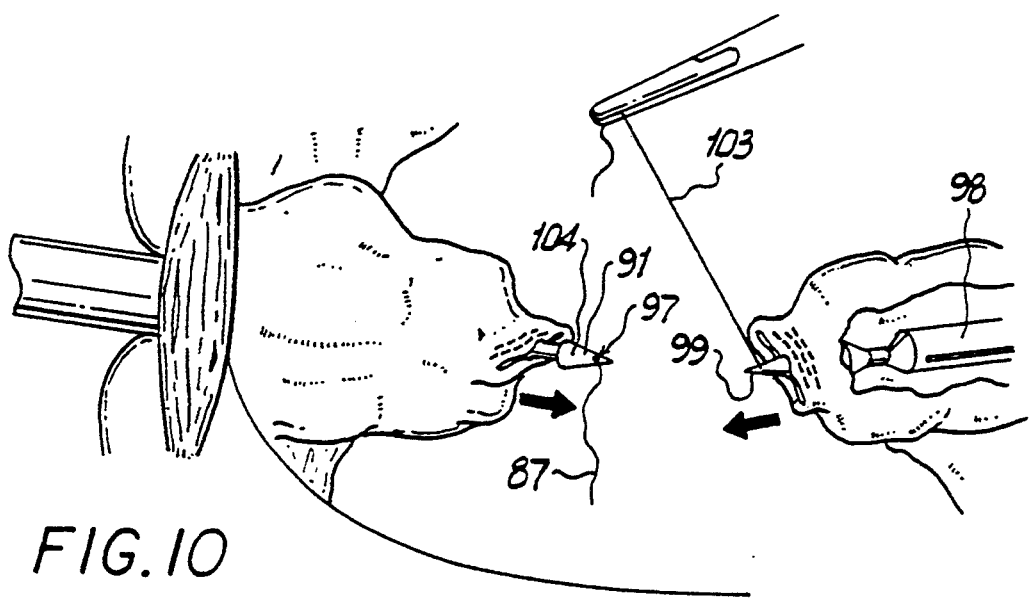
FIG. 10 is a perspective view showing the trocar points pulled through the stapled edges of the tissue.
Figure 11:
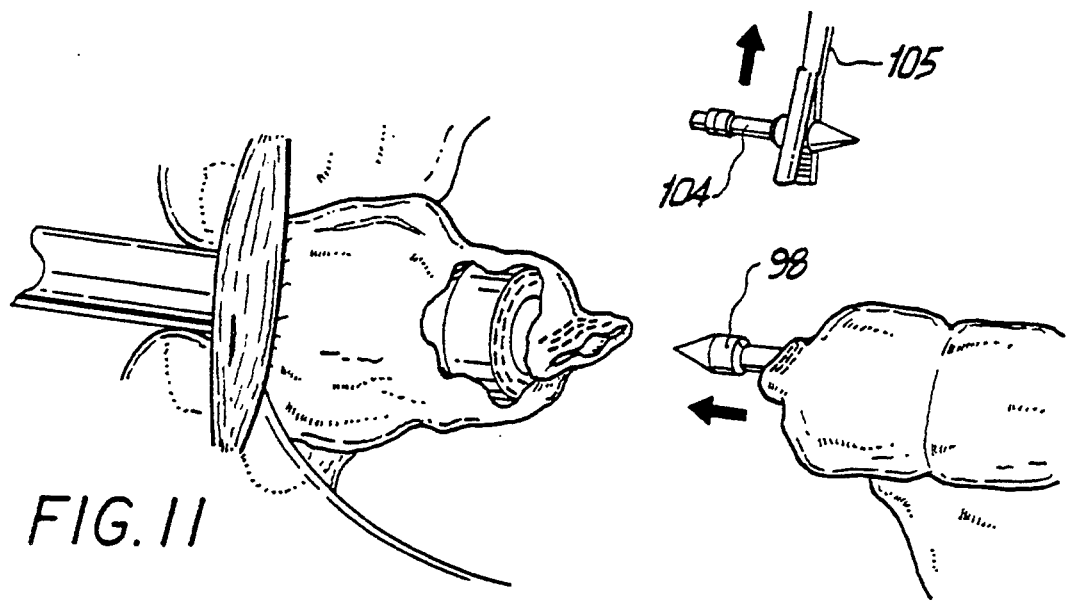
FIG. 11 is a perspective view showing a detachable trocar point being removed by grippers.

Referring to FIGS. 10 and 11, in this embodiment there is also provided a pointed trocar tip 104 having a suture or thread retaining hole 97 at a point 91 and an annular projection 93 at a proximal end thereof for snap fit insertion in the annular depression 102 of clamp rod 88.

In still a further embodiment of the invention a safety button 106, FIG. 3, is provided on saddle 20 for preventing handle 24 from being prematurely closed.

As can be seen in FIGS. 14(a-c) the knife blade 82 may have several cutting profiles designed to optimize a particular cutting operation. In these embodiments the leading edge of the knife blade 82 may have a flat shape (FIG. 14a), a sinusoidal shape (FIG. 14b) or a hyperbolic shape (FIG. 14c). It is within the contemplated scope of the invention to use varying knife blade profiles not limited to those shown herein.

Referring now to FIGS. 2-13 the sequence of operation of the present invention will now be described. In preparing ring applier 10 for use, outer ring 94 is placed over projection 92 of clamp rod 88. Retainer 96 is threaded over outer ring 94 securing outer ring 94 to clamp rod 88. Inner ring 72 is inserted into enlarged area 66 and abuts flange 68 of pusher 62. Intermediary ring 52 is then press fit into the grooved distal end 50 of external cap 48. In this manner, the ring applier 10 is readied for use.

Figure 9:
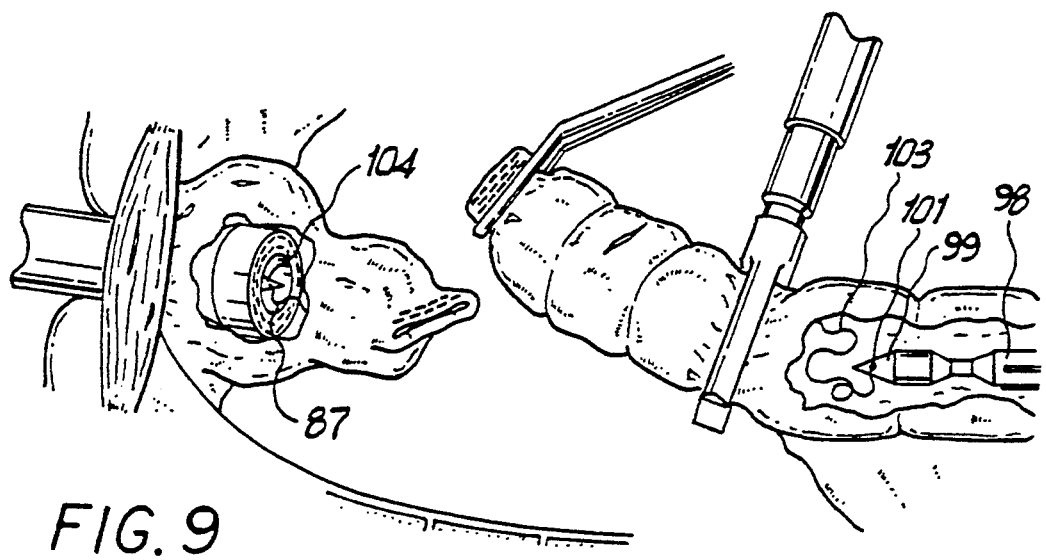
FIG. 9 is a perspective view of a diseased section of the colon being excised and showing a detachable portion of the instrument deployed in a distal section of the colon.

In a preferred use of the invention the detachable center rod 98 assembly including outer ring 94 and retainer 96, and a trailing suture 103 attached to a hole 101 of center rod tip 99, would have been inserted into a healthy section of tubular tissue and located distally from the diseased tissue FIG. 9. As further shown in FIG. 9, the diseased tissue would then be excised by known methods such as applying several staggered rows of staples about each end of diseased tissue and cutting and removing the diseased and now stapled "packet" of diseased tissue leaving two healthy free ends of tissue stapled closed.

Referring to FIG. 10, a small incision would then be made to grasp trailing suture 103 and pull pointed tip 99 of center rod 98 through the stapled section of tissue. With trocar tip 104 snap fit into place on clamp rod 88, tip 104 would be inserted up to the opposing stapled tissue end and pulled through the staples by a suture 87 affixed to hole 97 in point 91 in the same manner as above, as best seen in FIG. 17a.

Figure 12:
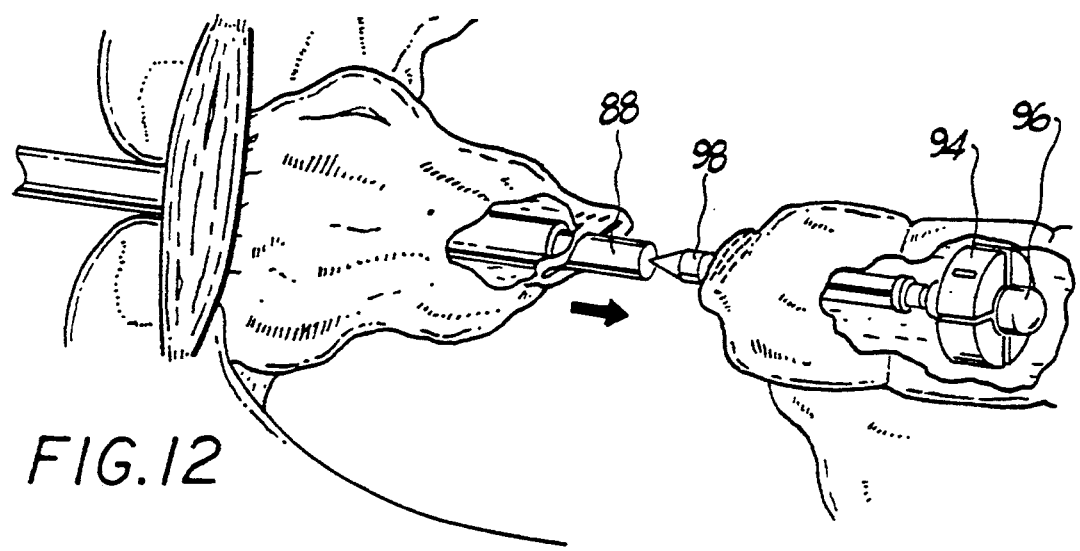
FIG. 12 is a perspective view showing the detachable assembly being attached to the instrument.
Figure 13:
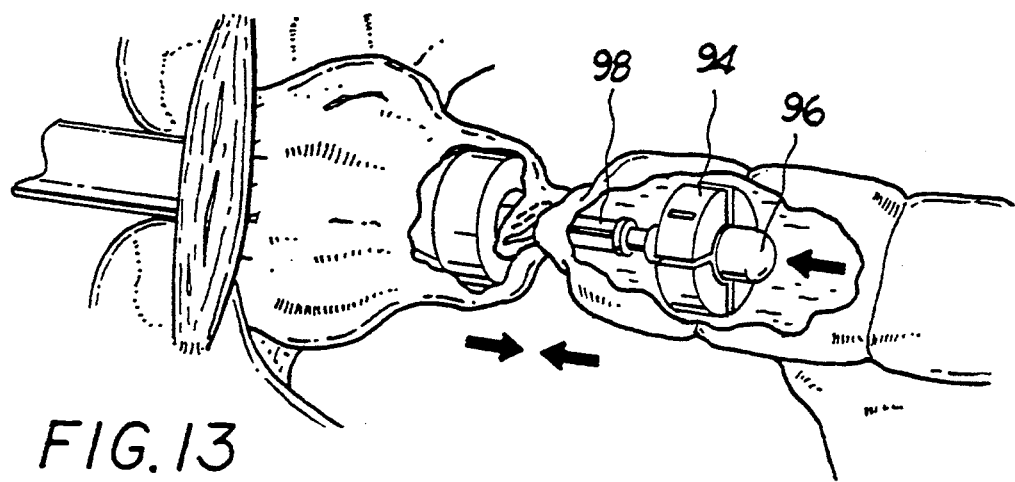
FIG. 13 is a perspective view of the colon just prior to clamping the ring assemblies.

As shown in FIG. 11, trocar tip 104 can then be removed from clamp rod 88 by grippers 105 or other known methods, after which clamp rod 88 is then snap fit over the proximal end of center rod 98 to attach center rod assembly 98 to clamp rod 88 of ring applier 10 FIGS. 12 and 13.

Once the two rods, 88 and 98, have been joined, with the stapled free ends of tubular tissue now located between outer ring 94 and intermediary ring 52 the clamp rod 88 is retracted by turning the clamp knob 34 which draws the threaded shaft 42 and thus the clamp rod 88 rearward. Drawing clamp rod 88 rearward pulls outer ring 94 over intermediary ring 52 thus clamping the free ends of the tubular tissue sections between rings 94 and 52.

The remaining operation can best be easily understood in stages wherein FIG. 4 is stage one showing outer ring 94 fully retracted over intermediary ring 52. The free ends of the tissue sections (not shown) would be captured between the rings 52 and 94. At the end of stage one the center of outer ring 94 and the excess tissue are ready to be cored by knife blade 82. In this stage it can be seen that pusher 62 and knife holder 74 are disposed fully to the rear of external cap 48 and shifter keys 84 reside between shifter key channels 64 in pusher 62 and shifter key recess 78 on knife holder 74. The positions of the base of knife holder 74 are indicated by reference letter A, the base of the pusher 62 by reference letter B, the forward edge of the knife blade 82 by reference letter C and the position of the shifter keys 84 are indicated by reference letter D.

Figure 5:
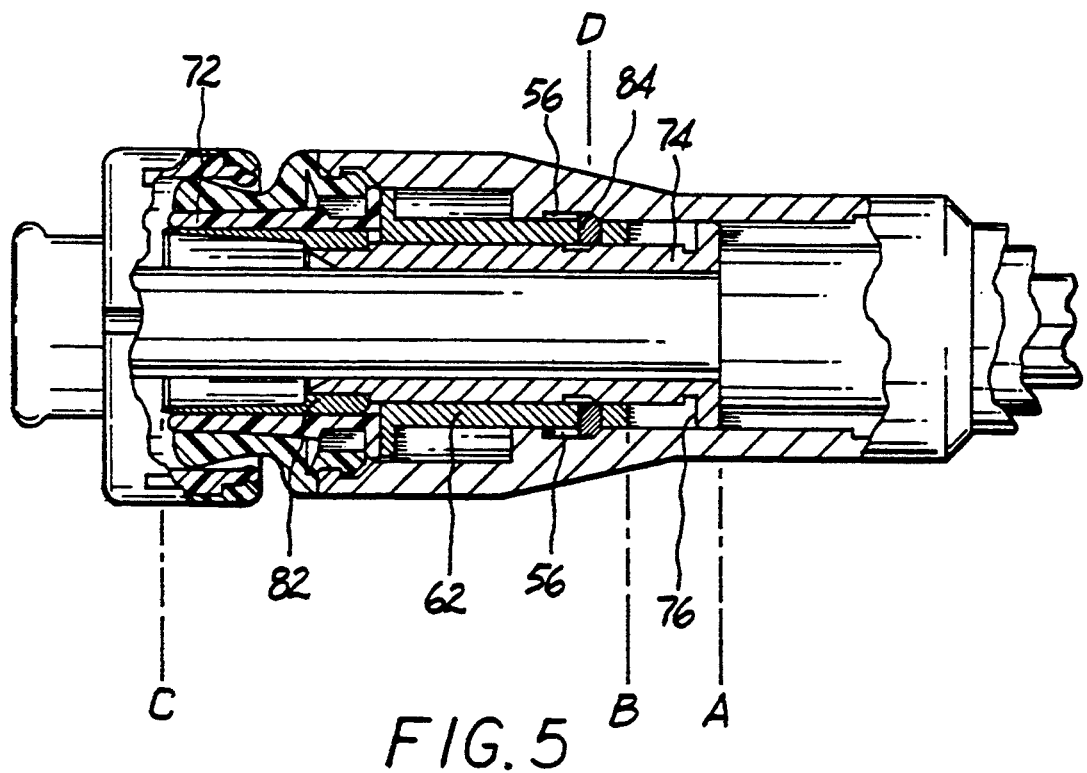
FIG. 5 is a similar view thereof showing insertion of an inner locking ring into said intermediary ring.

When the handles 42 are pivoted inward after the first stage knife tube 86 moves pusher 62 and knife holder 74 together as a unit, connected by said shifter keys, forward. Pusher 62 thus moves inner ring 72 forward into locking engagement with intermediary ring 52 at which point (stage 2) the shifter keys 84 are forced out of shifter key recesses 78 and into dwell recesses 56 (Reference point D) due to the angles on the edges of shifter keys 84 and shifter key recesses 78. As can be seen in FIG. 5, at the end of the second stage the end of pusher 62 (reference point B) and the end of the knife holder 74 (reference point A) are still spaced apart.

Figure 6:
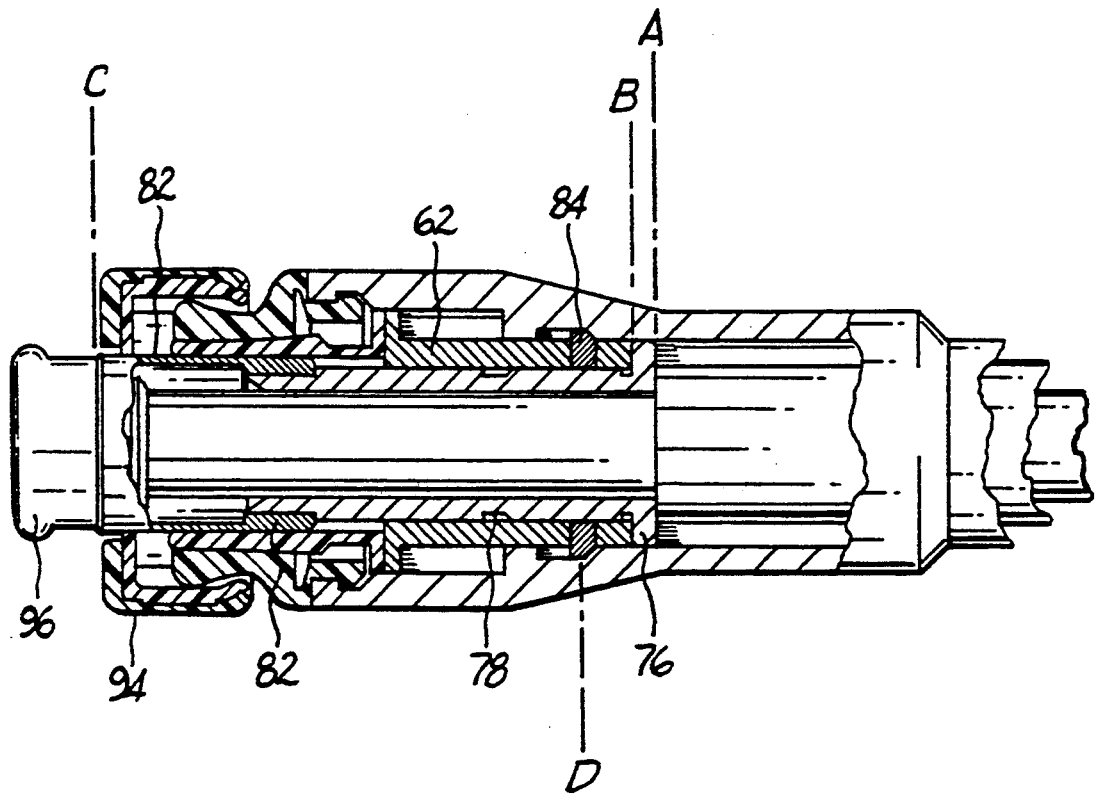
FIG. 6 is a similar view thereof showing the advancement of the coring means through the outer ring.

Referring to FIG. 6, in stage 3 handles 24 continue to pivot and knife tube 86 advances knife holder 74, independent of pusher 62 which is disengaged from knife holder 74, until rear flanges 76 on said knife holder 74 (reference point A) abut the rear edge of the pusher 62 (reference point B). During stage 3 advancing knife holder 74 advances knife blade 82 (reference point C) through the captured excess tissue and through the portion of outer ring 94 held by retainer 96 thus fully coring the multi-ring clamp assembly to provide a clear passageway therein.

It will be noted that with shifter keys 84 positioned in dwell recess 56 there is nothing to advance the pusher 62 until the end of stage 3 wherein said knife holder flange 76 abuts the rear end of pusher 62.

Figure 7:
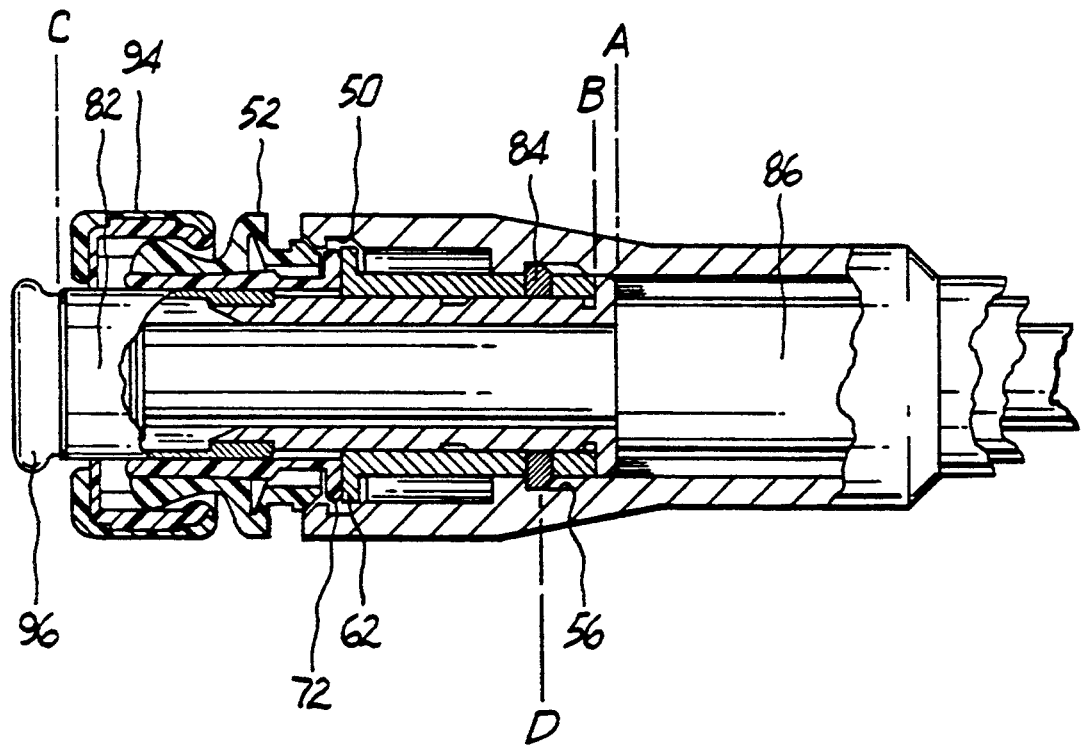
FIG. 7 is a similar view thereof showing the release of the coupling assembly from the present invention.

Finally, as can best be seen in FIG. 7 (stage 4) as handles 24 are pivoted fully closed flange 76 of knife holder 74 (reference point A) is moved forward by knife tube 86 carrying with it pusher 62 (see reference point B). Shifter keys 84 now move forward in dwell recesses 56 allowing pusher 62 to finally push the assembled rings free of the annular holding groove 50 on external cap 48. At this point the rings have been fully assembled about the free ends of the tissue sections, excess tissue and the center of outer ring 94 have been cored out leaving a clear passageway therein and the assembled rings are freed from ring applier 10. Thus the use of the shifter keys and dwell recesses allows the coring operation to be fully complete before the ring assembly is pushed free of the instrument. Ring applier 10 can now be removed. Eventually the clamped tissue will necrotize while the tubular tissue ends heal together. The necrotized tissue and ring assembly will then detach from the healthy tissue and be expelled from the body.

As described above, in a preferred use of the invention the ring assembly is of the fragmentable variety to facilitate expulsion. Furthermore, whether of the solid or fragmentable variety, the ring assembly may be partially or wholly formed of degradable or bio-absorbable materials which are degraded or absorbed over time as the tissue heals leaving less or no clamp material to be expelled by the body.

An alternative embodiment of the present invention is illustrated in FIGS. 15 and 23 wherein ring applier 200 generally includes a body portion 202, a head portion 204 and a retractor portion 206 extending through body portion 202 and head portion 204.

As shown in FIGS. 15 and 23, body portion 202 is comprised of an elongated front end tube 208, preferably curved, having a bore 210 therein and a wing shaped back end 212 having a bore 214 coaxial with bore 210. Body 202 includes a pair of handles 216, pivotally and opposingly mounted on body wing 212, having inwardly extending front ends 218 extending into wing bore 2141. A knife cam 220 is slidingly disposed within wing bore 214 and in abutting contact with inwardly extending front ends 218 such that pivoting handles 216 inward forces knife cam 220 forward within wing bore 214.

Body portion 202 further includes a tail member 222, defining a bore 224 coaxial and communicable with wing bore 214, which extends backwards from body wing 212 and is centered between opposing handles 216. A barrel 226, defining a bore 228, is rotatably attached to body wing 212 at a first end and is rigidly affixed to tail bore 224 at a second end for rotatable support tail member 222 on body wing 212.

A clamp cam 230 having a variable helical depression 232 on an outer surface thereof, and defining a bore 233 is rotatably suspended within barrel bore 228. The variable helical depression 232 in cam 230 is initially of a slow rate of twist at a proximal end of cam 230 to provide a rapid initial approximation of rings 52 and 94. At the distal end of cam 230 the helical depression 232 changes to a rapid rate of twist to provide slower more precise approximation of rings 52 and 94 and to provide increased torque for clamping rings 52 and 94 around ends of tubular tissue sections.

A guide tube 234 is affixed to wing body 212 at a first end and extends through bore 233 on clamp cam 230 into tail bore 224 to guide clamp cam 230 within tail bore 224.

A guide pin 236 is rigidly affixed to barrel 226 at a proximal end thereof and extends into barrel bore 228 such that a free end of pin 236 engages the helical depression 232 of clamp cam 230. By rotating tail member 222, barrel 226 drives pin 236 in helical depression 232, thereby drawing clamp cam 230 along guide rod 234 initially at a fast rate and subsequently in a slower, stronger and more precise fashion.

Referring to FIGS. 17, 18 and 23 head portion 204 is similar to head portion 14 referred to above and contains the same parts/elements recited therein including pusher 62, knife holder 74, knife blade 82 and shifter keys 84 which function together in exactly the same manner recited hereinabove. As shown in FIG. 18a in one embodiment of ring applier 200 external cap 48 is integral with front end tube 208. In a second embodiment of ring applier 200, FIG. 18b, external cap 48 is partially integral with tube 208 and has a threadably detachable front portion 201 to facilitate insertion of the rings. In a third embodiment of ring applier 200, FIGS. 17a and 17b, external cap 48 is affixed to body tube 208 by a threaded sleeve-head 203 threaded into external cap 48.

As shown in FIGS. 17b, 18b and 23, a pair of abutting semicircular guide inserts 238 are disposed within tube bore 210 and extend therethrough. Each insert 238 has a pair of longitudinally extending grooves along each of their respective longitudinal edges such that, when paired in abutting relation to form a complete tube, the inserts 238 define inner 240 and outer 242 pairs of coaxial and longitudinally extending channels in inserts 238.

A pair of knife bands 244 are slidably supported within outer channels 242 and extend therethrough. Knife bands 244 are affixed to knife cam 220 at a proximal end and to knife holder 74 at a distal end such that pivoting handles 216 slides knife holder 74 within pusher 62 thereby transmitting the motion through tube 208.

Referring to FIGS. 17a and 17b retractor portion 206 includes a shortened clamp rod 248 extending into external cap 48 at a proximal end thereof and having the leaf-spring snap-fit type of engagement with center rod assembly 98 referred to above in ring applier 10 and is supplied with a similar trocar tip 104, FIG. 17c.

As shown in FIGS. 18a and 18b, in a second embodiment of shortened clamp rod 248, an annular projection 250 on clamp rod 248 engages an annular depression 252 on center rod 98 for a snap-fit type of engagement similar to that of the first embodiment but without a plurality of leaf springs 95. A pair of trocar points 254 and 256 similar to those mentioned above are provided for snap-fit connection to clamp rod 248 and annular depression 252 on center rod 98 respectively.

Referring to FIGS. 17b, 18b and 23, retractor portion 206 further includes a pair of clamp bands 246 slidably suspended within inner channels 240 and attached at distal ends thereof to clamp rod 248. Bands 246 are affixed to clamp cam 230 at proximal ends thereof such that turning tail member 222 moves clamp cam 230 and thus center rod assembly 98 thereby transmitting the motions of cam 230 through tube 208 to center rod assembly 98.

Figure 16:
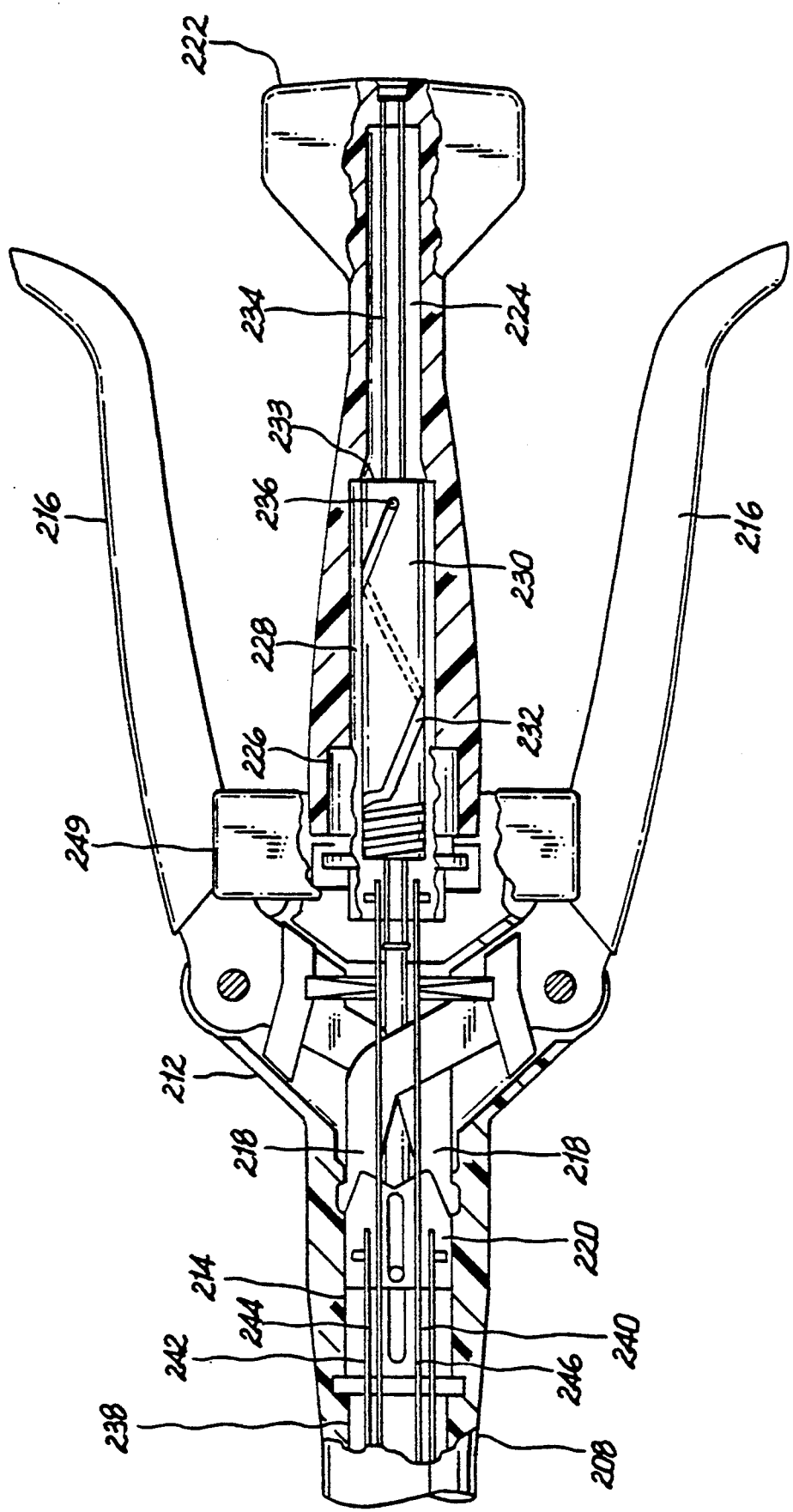
FIG. 16 is a side detail view of the handle portion of the alternative embodiment.
Figure 19A:
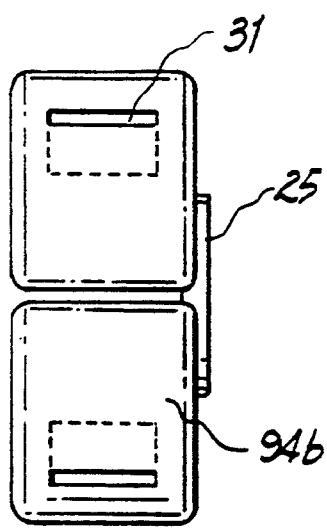
FIGS. 19 (a-e) are detail views of a female outer ring.
Figure 19B:
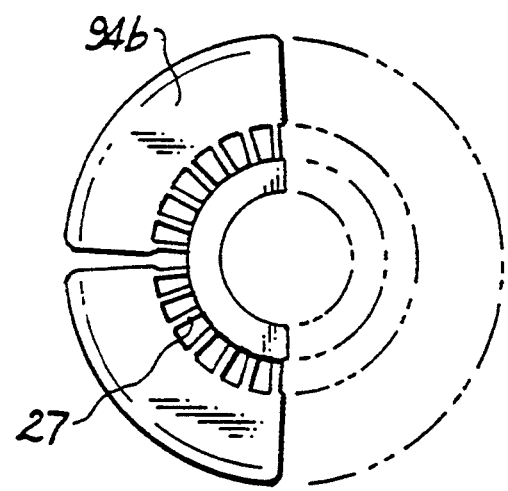
Figure 19C:
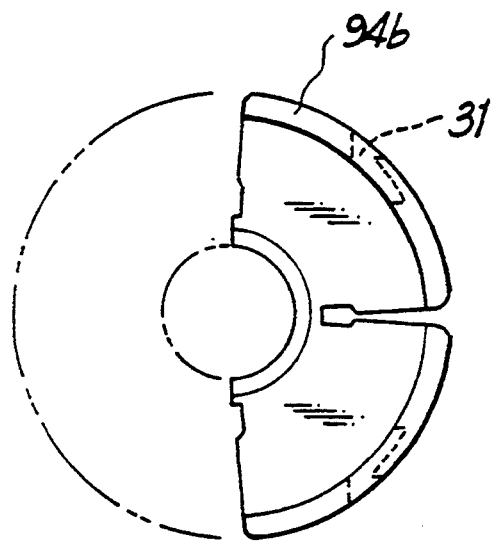
Figure 19D:
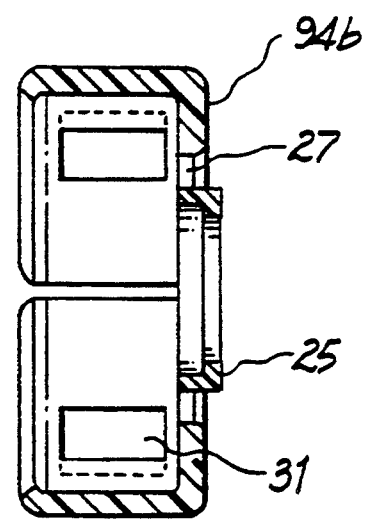
Figure 19E:
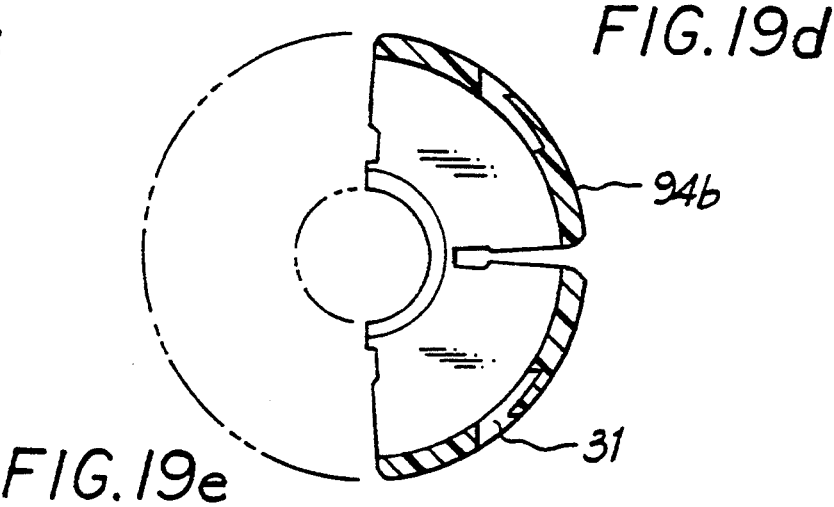
Figure 20A:
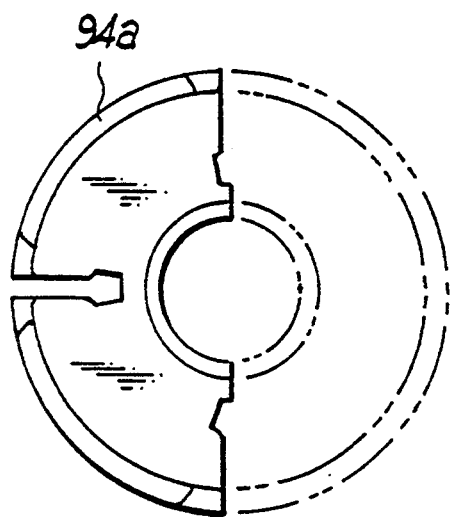
FIGS. 20 (a-e) are detail views of a male outer ring.
Figure 20B:
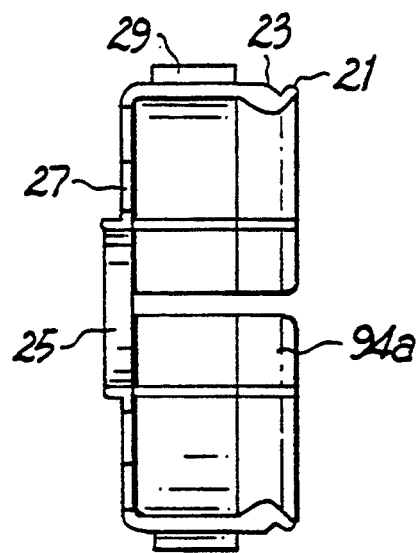
Figure 20C:
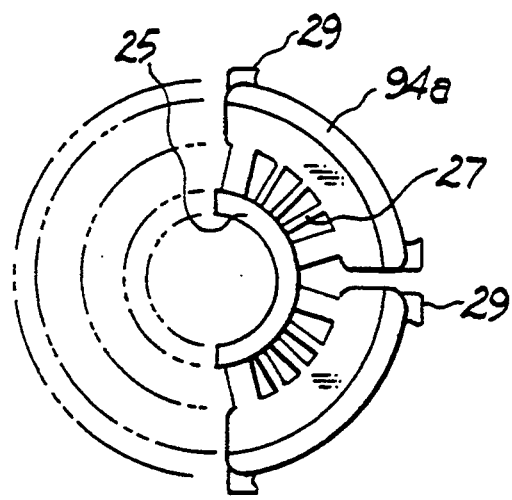
Figure 20D:
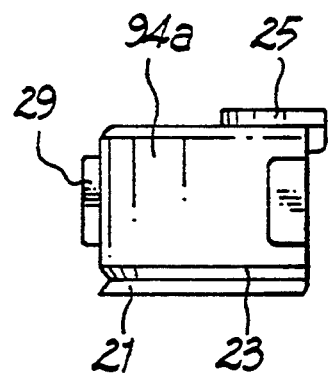
Figure 20E:
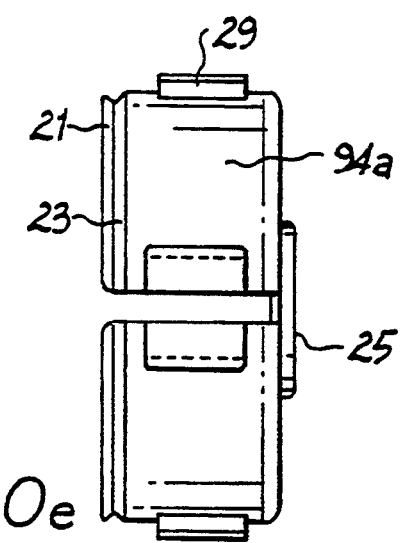

Referring to FIGS. 15, 16, and 23 ring applier 200 is preferably provided with a wing safety 249 rotatably mounted on wing body 212 and positioned between handles 216 such that safety 249 blocks movement of handles 216 in a first position and allows free movement of handles 216 when safety 249 is rotated to a second position.

In use, ring applier 200 is readied and operated in similar fashion to ring applier 10. In one embodiment of ring applier 200, after center rod assembly 98 has been deployed in a distal section of tubular tissue, both trocar tips 254 and 256 are removed from the surgical field by grippers 105 prior to attaching center rod assembly 98 to clamp rod 250 as shown in FIG. 18b.

Turning tail member 222, analogous to the turning of clamp knob 34 above, draws helical cam 230 rearward initially a rapid rate to provide quick approximation of rings 52 and 94 and subsequently at a slower rate for more precise approximation of rings 52 and 94. Increased torque accompanies the slower approximation rate to apply a higher clamping force between rings 52 and 94 and the tissue section clamped therebetween.

Pivoting handles 216 is analogous to the pivoting of handle 42 above in that the knife holder 74 is forced forward to initially insert locking inner ring 72 into intermediary ring 52, subsequently core the ring assembly and thereafter finally push the multi-ring assembly and clamped tissue free of ring applier 200.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A method of affixing a multi-ring clamping device to a first and a second section of tubular tissue comprising:
   a) inserting an outer ring assembly supported on an insertion tool into said first tissue section;
   b) positioning inner and intermediary ring assemblies carried by said insertion tool within said second tissue section;
   c) retracting said outer ring assembly over said intermediary ring assembly such that said outer ring assembly substantially surrounds said intermediary ring assembly to hold said tissue sections therebetween;
   d) advancing a pusher to push said inner ring assembly into locking engagement within said intermediary ring assembly;
   e) advancing a blade independently of said pusher to cut an amount of excess clamped tissue and a central portion of said ring assemblies; and
   f) pushing said ring assembly from said insertion tool.

2. The method of affixing a multi-ring clamping device to a first and a second section of tubular tissue as recited in claim 1 further comprising:
   providing an apparatus having support means for carrying and aligning a plurality of ring assemblies; driving means for applying said plurality of ring assemblies to tissue sections; channeling means for coring excess clamped tissue and centers of said ring assemblies; releasing means for freeing said rings from said support means; and, dwell means for advancing said channeling means independently of said releasing means.

3. A surgical instrument for application of multi-ring clamping devices, of the type having a plurality of ring assemblies, for compression anastomosis of a first and second tubular tissue section, said apparatus comprising:
   a) support means for carrying and aligning a plurality of ring assemblies;
   b) driving means at least partially disposed within said support means for applying said plurality of ring assemblies to the first and second tissue sections;
   c) channeling means operatively associated with said driving means for coring excess clamped tissue;
   d) releasing means engageable with said channeling means for freeing said plurality rings from said support means after clamping said tissue; and
   e) dwell means associated with said releasing means and said channeling means for alternately engaging and disengaging said releasing means with said channeling means, wherein said releasing means are engaged with said channeling means during application of said plurality of ring assemblies to the first and second tissue sections and said releasing means are disengaged from said channeling means during coring.

4. The surgical instrument as recited in claim 3 wherein said multi-ring clamping device includes an intermediary ring assembly, an outer ring assembly and an inner ring assembly and said support and aligning means includes:
   a) a body tube;
   b) an external cap affixed to a distal end of said body tube and having means for support of said intermediary ring assembly;
   c) inner transmission means slidably located within, and coaxial to, said body tube including means to support said outer ring assembly; and
   d) outer transmission means coaxial with, and slidably positioned between, said body tube and said inner transmission means including means for supporting said inner ring assembly.

5. The surgical instrument as recited in claim 4 wherein said inner transmission means comprises a clamp rod and said outer transmission means comprises a knife tube.

6. The surgical instrument as recited in claim 4 wherein said inner transmission means comprises:
   a) a guide tube, coaxial with and affixed to an inner surface of said body tube, defining a plurality of inner and outer longitudinally extending channels therein; and
   b) at least one clamp band slidably disposed within said inner channels.

7. The surgical instrument as recited in claim 6 wherein said outer transmission means comprises at least one knife band slidably disposed within said outer channels.

8. The surgical instrument as recited in claim 4, wherein said driving means further comprises:

a) retracting means for drawing said outer ring assembly over said intermediary ring assembly capturing said tissue sections therebetween; and b) advancing means for pushing said inner ring assembly into locking engagement with said intermediary ring assembly.

9. The surgical instrument as recited in claim 8 wherein said retraction means includes means for retracting said inner transmission means.

10. The surgical instrument as recited in claim 9 wherein said means for retracting said inner transmission means includes a clamp knob having a threaded bore section for engagement with a proximal end section of said inner transmission means.

11. The surgical instrument as recited in claim 9 wherein said means for retracting said inner transmission means includes:

a) a barrel having an inward facing projection, said barrel being rotatably mounted with respect to said body tube;

b) a tail member affixed to said barrel; and c) a clamp cam slidably disposed within said barrel and having a variable helical depression on an exterior surface thereof engagable with said barrel projection, said clamp cam affixed to a proximal end of said inner transmission means such that turning said tail member drives said projection within said helical depression thereby moving said inner transmission means within said body tube.

12. The surgical instrument as recited in claim 8 wherein said advancing means includes means for advancing said outer transmission means.

13. The surgical instrument as recited in claim 12 wherein said means for advancing said outer transmission means includes:

a) a saddle body; and b) at least one handle member pivotably affixed to said saddle body and having a first end extending into said saddle body engaging a proximal end of said outer transmission means such that pivoting said handle moves said outer transmission means within said body tube.

14. The surgical instrument as recited in claim 4 wherein said means for support of said intermediary ring assembly includes an annular groove around an inside lip of said external cap for snap fit engagement with an edge of said intermediary ring assembly.

15. The surgical instrument as recited in claim 4 wherein said means to support said outer ring assembly includes a clamp rod having an annular projection on a threaded first end thereof and attached to a distal end of said inner transmission means at a second end thereof, said clamp rod further including a threaded retainer cap for threaded engagement with said threaded clamp rod end such that said outer ring assembly may be held between said annular projection and said retainer cap.

16. The surgical instrument as recited in claim 4 wherein said means for supporting said inner ring assembly includes a pusher slidably disposed within said external cap such that said inner ring assembly abuts a distal end of said pusher when disposed within a bore of said external cap.

17. The surgical instrument as recited in claim 4 wherein said channeling means includes a knife blade for coring excess tissue and a center area of said ring assemblies and further includes means for advancing said blade.

18. The surgical instrument as recited in claim 17 wherein said means for advancing said knife blade includes a knife holder detachably affixed to said knife blade and in engagement with a distal end of said outer transmission means.

19. The surgical instrument as recited in claim 17 wherein a leading edge profile of said knife blade is sinusoidal.

20. The surgical instrument as recited in claim 17 wherein said knife blade leading edge profile is hyperbolic.

21. The surgical instrument as recited in claim 4 wherein said releasing means includes a pusher having an outward projecting circumferential flange at a distal end of said pusher, and a plurality of shifter key channels extending through said pusher, such that advancement of said pusher within said external cap pushes said intermediary ring assembly free of said external cap.

22. The surgical instrument as recited in claim 21 wherein said dwell means includes:

a) a plurality of shifter keys slidably disposed in said shifter key channels;

b) a plurality of dwell recesses on an inner surface of said external cap; and c) a plurality of shifter key recesses on an outer surface of said channeling means such that said shifter keys reside between said shifter key channels and said dwell recess during said coring thereby disengaging said pusher from said channeling means, thereafter said channeling means acting directly on said pusher to force said multi-ring compression device from said instrument.

23. A surgical instrument for application of multi-ring clamping devices for compression anastomosis of a first and second tubular tissue section comprising:

a) a multi-ring clamping device having a plurality of ring assemblies;

b) support means for carrying and aligning said plurality of ring assemblies;

c) driving means for driving said support memos for clamping a first and a second tissue section between at least two of said ring assemblies;

d) channeling means .operatively associated with said driving means for coring an amount of excess clamped tissue and at least a portion of at least one of said ring assemblies;

e) releasing means engageable with said channeling means for freeing said ring assemblies having tissue clamped therebetween from said instrument; and f) dwell means associated with said channeling means and said releasing means for alternately engaging and disengaging said releasing means with said channeling means, wherein said releasing means is engaged with said channeling means during application of said plurality of ring assemblies to tissue sections and said releasing means are disengaged from said channeling means during coring.

24. A surgical instrument for application of multi-ring clamping devices, of the type having at least a first and a second ring assembly, for compression anastomosis of a first and second tubular tissue section, said apparatus comprising:

a) support means for carrying and aligning a first and second ring assembly;

b) driving means for driving said support means for applying said first and second ring assemblies to tissue sections;

c) channeling means operatively associated with said driving means for coring excess tissue clamped between said first and said second ring assemblies;
d) releasing means engageable with said channeling means for freeing said second ring assembly from said support means after clamping said tissue;
e) means associated with said channeling means and said releasing means for disengaging said releasing means from said channeling means during coring; and
f) means for detaching said means for support of said first ring assembly from said means for support of said second ring assembly.

25. The surgical instrument as recited in claim 24 wherein said detaching means comprises:
a) a center rod for supporting said outer ring assembly and having an annular projection at a proximal end thereof; and
b) wherein said driving means includes a clamp rod having an annular recess at a distal end thereof and a plurality of leaf springs disposed in said recess for snap fit engagement with said annular projection.

26. A surgical instrument for installation of multi-ring clamping devices having a plurality of ring assemblies for compression anastomosis of a first and a second tubular section comprising:
a) an external tube;
b) an external cap, affixed to a distal end of said external tube, having an annular groove at a distal end for retention of at least an intermediary ring assembly and a plurality of dwell recesses on an inner surface of said external cap, said external cap enclosing;
   i) a pusher adapted to support at least an inner ring assembly within said external cap, said pusher having an outwardly extending circumferential flange at a distal end thereof, and located within said external cap, said pusher further having a plurality of shifter key channels extending transversely therethrough;
   ii) a knife holder, located coaxially within said pusher, having a base flange at a proximal end and a plurality of shifter key recesses located on an outer surface thereof;
   iii) a knife blade affixed to a distal end of said knife holder;
   iv) a plurality of shifter keys residing in said shifter key channels and engagable with said shifter key recesses and said dwell recesses;
c) a body case affixed to a proximal end of said external tube, said body case including;
   i) a knife tube partially located within said external tube, a distal end of said knife tube engaging, a proximal end of said knife holder and a proximal end of said knife tube extending into said body case;
   ii) a handle pivotably mounted on said body case, said proximal end of said knife tube affixed to an end of said handle;
   iii) a clamp knob having a threaded bore rotatably supported on said body case and having a threaded nut slidably disposed therein;
   iv) a safety button springingly biased within said handle for blocking engagement of said handle in a first position and releasing engagement in a second position;
d) an inner rod at least partially disposed within said external tube comprising:
   i) a center rod having means for retaining an outer ring assembly on a distal end thereof and an annular projection at a proximal end thereof; and
   ii) a clamp rod engageable with said center rod and located within said knife tube, said clamp rod having an annular depression at a distal end thereof for snap fit engagement with said annular projection and a threaded surface at a proximal end engagable with said threaded clamp knob and said nut, such that turning said clamp knob draws said threaded clamp rod rearward causing said outer ring assembly to be retracted over said intermediary ring assembly to clamp tissue sections therebetween, when said handle is initially pivoted;

said shifter keys engage said shifter key recesses and said knife tube and knife holder drive said pusher and thus said inner ring assembly into locking engagement with said intermediary ring assembly; when said handle is partially further pivoted; said shifter keys are forced outward into said dwell recesses allowing said knife holder to be driven forward independent of said pusher, said knife blade cutting said clamped tissue sections and an inner area of said ring assemblies until said knife holder base flange abuts a proximal end of said pusher at which point when said handle is finally further pivoted said shifter keys advance forward in said dwell recesses allowing said pusher to force said multi-ring clamping device free of said external cap.

27. A surgical instrument for installation of multi-ring clamping devices having a plurality of ring assemblies for compression anastomosis of a first and a second tubular section comprising:
a) an external tube;
b) an external cap, affixed to a distal end of said external tube, having an annular groove at a distal end for retention of at least an intermediary ring assembly and a plurality of dwell recesses on an inner surface of said external cap, said external cap enclosing;
   i) a pusher for supporting an inner ring assembly within said external cap, said pusher having an outwardly extending circumferential flange at a distal end, located within said external cap and having a plurality of shifter key channels extending transversely therethrough;
   ii) a knife holder, located coaxially within said pusher, having a base flange at a proximal end, said knife holder having a plurality of shifter key recesses located on an outer surface thereof;
   iii) a knife blade affixed to a distal end of said knife holder;
   iv) a plurality of shifter keys residing in said shifter key channels and engagable with said shifter key recesses during a clamping stroke and engagable with said dwell recesses during coring and releasing strokes;
c) a body case affixed to a proximal end of said external tube, said body case including;
   i) a pair of guide inserts, defining a plurality of guide channels, positioned within said external tube and partially extending into said body case;
   ii) a pair of knife bands located within said guide channels, a distal end of said knife bands engaging said proximal end of said knife holder and a proximal end of said knife bands extending into said body case;

iii) a pair of handles pivotably mounted on said body case and having free ends extending into said body case:

iv) a knife cam slidably disposed within said body case, a proximal end of said knife cam in abutting contact with said handle free ends and a distal end of said knife cam affixed to said proximal end of said knife bands;

v) a clamp knob, having a bore, rotatably supported on said body case and having a helical clamp cam slidably disposed therein adapted to slide within said bore as said knob is rotated;

vi) a rotatable safety lever on said handle for blocking engagement of said handle in a first position and releasing engagement in a second position;

vii) a pair of clamp bands slidably disposed within said guide channels, a proximal end of said clamp bands affixed to said helical clamp cam;

d) a clamp rod, located within said external cap and extending outward therefrom, having an annular depression at a distal end thereof, a proximal end of said clamp rod engageable with a distal end of said clamp bands; and e) a center rod engageable with said clamp rod and having means for retaining an outer ring assembly on a distal end thereof, said center rod having an annular projection at a proximal end thereof for snap fit engagement with said annular depression;

wherein turning said clamp knob draws said clamp band rearward causing said outer ring assembly to be retracted over said intermediary ring assembly, when said handle is initially pivoted;

said shifter keys engage said shifter key recesses and said knife band and knife holder drive said pusher and thus said inner ring assembly into locking engagement with said intermediary ring assembly to clamp said tissue sections therebetween; when said handle is then further pivoted; said shifter keys are forced outward into said dwell recesses allowing said knife holder to be driven forward independent of said pusher, said knife blade cutting said clamped tissue sections and an inner area of said ring assemblies until said knife holder base flange abuts said pusher at which point when said handle is finally pivoted; said shifter keys advance forward in said dwell recesses allowing said pusher to force said multi-ring clamping device free of said external cap.

28. A surgical instrument for application of surgical fasteners, of the type having a plurality of ring members, to fasten a first tubular tissue section and to a second tubular section comprising:

a) a frame portion;

b) retraction means at least partially within said frame portion and movable relative to said frame portion for approximating a first tissue section and a second tissue section therebetween;

c) pushing means at lest partially disposed within said frame portion for application of surgical fasteners in surrounding relation with respect to each other to fasten the first tissue section to the second tissue section;

d) channeling means engagable with said pushing means for coring an amount of excess tissue captured between the surgical fasteners; and e) dwell means associated with said pushing means and said channeling means for advancing said channeling means independently of said pushing means, wherein the ring members are applied to the first and second tissue sections in surrounding relation to fasten the first tissue section to the second tissue section.

29. The surgical instrument as recited in claim 28 wherein said dwell means includes means for engaging and disengaging said channeling means with said pushing means, such that said pushing means is engaged with said channeling means during application of the surgical fasteners and said pushing means is disengaged from said channeling means during said coring.

30. The surgical instrument as recited in claim 29 wherein said dwell means comprises a shifter member movable between said pushing means and said channeling means for engagement and disengagement of said pushing means with said channeling means.

31. A surgical instrument for application of surgical fasteners, of the type having a plurality of ring members, to fasten a first tubular tissue section and to a second tubular tissue section comprising:

a) frame portion;

b) retraction means at least partially disposed within said frame portion and movable relative to said frame portion for approximating a first tissue section and a second tissue section therebetween;

c) pushing means at least partially disposed within said frame portion for application of surgical fasteners to fasten the first tissue section to the second tissue section;

d) channeling means engagable with said pushing means for coring an amount of excess tissue captured between the surgical fasteners; and e) dwell means associated with said pushing means and said channeling means for advancing said channeling means independently of said pushing means, said dwell means comprising a shifter member movable between said pushing means and said channeling means for engagement and disengagement of said pushing means with said channeling means, wherein said shifter member resides within said pushing means and is movable with respect thereto, said shifter member being movable into and out of a recess in said channeling means, such that the ring members are applied to the first and second tissue sections in overlapping relation to fasten the first tissue section to the second tissue section.

32. A surgical instrument for application of surgical fasteners to fasten a first tubular tissue section and to a second tubular tissue section, said fasteners including a plurality of anastomosis rings, said instrument comprising:

a) frame means for support of an intermediary ring;

b) retraction means at least partially disposed within said frame means for support of an outer ring, said retraction means further including means for drawing said outer ring over said intermediary ring to capture a first tissue section and a second tissue section therebetween;

c) channeling means at least partially disposed within said frame portion for coring excess tissue captured between said intermediary ring and said outer ring:

d) pushing means engagable with said channeling means for pushing an inner ring into locking engagement with said intermediary ring and to release said intermediary ring free of said frame means; and e) dwell means associated with said pushing means for releasing said pushing means from said channeling means during coring.

33. The surgical instrument as recited in claim 32 wherein said dwell means includes a shiftable member, said shiftable member movable between a first position engaging said pushing means with said channeling means and a second position disengaging said pushing means from said channeling means.

34. The surgical instrument as recited in claim 32 further comprising driving means at least partially disposed within said frame means for moving said channeling means relative to said frame means.

35. A surgical instrument for application of multi-ring clamping devices, of the type having an intermediary ring assembly, an outer ring assembly and an inner ring assembly, for compression anastomosis of a first and second tubular tissue section said apparatus comprising:
   a) support means for carrying and aligning a multi-ring clamping device, wherein said support and aligning means includes:
      i) a body tube having means for support of an intermediary ring assembly;
      ii) inner transmission means located within, and coaxial to, said body tube, said inner transmission means including means to support an outer ring assembly, wherein said inner transmission means further includes:
         A) a guide tube, coaxial with and affixed to an inner surface of said body tube, defining a plurality of longitudinally extending channels therein; and
         B) at least one clamp band slidably disposed within said channels,
   b) driving means for driving said support means for applying said multi-ring clamping device to first and second tissue section;
   c) channeling means operatively associated with said support means for coring excess clamped tissue;
   d) releasing means engagable with said driving means for freeing said multi-ring clamping device from said support means; and
   e) dwell means associated with said releasing means for alternately engaging said releasing means with said channeling means.

36. A surgical instrument for application of multi-ring clamping devices, of the type having an intermediary ring assembly, an outer ring assembly and an inner ring assembly, for compression anastomosis of a first and second tubular tissue section said apparatus comprising:
   a) support means for carrying and aligning a multi-ring clamping device, said support means including;
      i) a body tube;
      ii) inner transmission means slidably located within, and coaxial to, said body tube including means to support said outer ring assembly, wherein said means to support said outer ring assembly includes a clamp rod having an annular projection on a threaded first end thereof and attached to a distal end of said inner transmission means at a second end thereof, said clamp rod further including a threaded retainer cap for threaded engagement with said threaded clamp rod end such that said outer ring assembly may be held between said annular projection and said retainer cap;
   b) driving means for driving said support means for applying said multi-ring clamping device in surrounding relation to first and second tissue sections;
   c) channeling means engagable with said driving means for coring excess clamped tissue;
   d) releasing means engagable with said driving means for freeing said multi-ring clamping device from said support means; and
   e) dwell means associated with said releasing means for alternately engaging said releasing means with said channeling means.

37. A surgical instrument for application of multi-ring clamping devices, of the type having a plurality of ring assemblies, for compression anastomosis of a first and second tubular tissue section said apparatus comprising:
   a) support means for carrying and aligning a multi-ring clamping device, said multi-ring clamping device including an intermediary assembly, an outer ring assembly and an inner ring assembly, said support means including means for support of said outer ring assembly and means for support of said inner ring assembly and said intermediary ring assembly;
   b) driving means for driving said support means for applying said multi-ring clamping device to first and second tissue sections;
   c) channeling means engagable with said driving means for coring excess clamped tissue;
   d) releasing means engagable with said driving means for freeing said multi-rings clamping device from said support means; and
   e) means associated with said support means for detaching said means for support of an outer ring assembly from said means for support of an intermediary and an inner ring assemblies, wherein said detaching means includes;
      i) a center rod for supporting said outer ring assembly and having an annular projection at a proximal end thereof; and
      ii) a clamp rod having an annular recess at a distal end thereof and a plurality of leaf springs disposed in said recess for snap fit engagement with said annular projection.

* * * * *